US012623077B2

(12) United States Patent
Law et al.

(10) Patent No.:     US 12,623,077 B2
(45) Date of Patent:          May 12, 2026

(54) NEUROMODULATOR APPARATUSES COMPRISING LED DRIVER INTEGRATED CIRCUITS

(71) Applicant: THYNC GLOBAL, INC., Los Gatos, CA (US)

(72) Inventors: Wing Law, Cupertino, CA (US); Remi Demers, Saint-Nicolas (CA)

(73) Assignee: THYNC GLOBAL, INC., Los Gatos, CA (US)

( * ) Notice: Subject to any disclaimer, the term of this patent is extended or adjusted under 35 U.S.C. 154(b) by 920 days.

(21) Appl. No.: 17/634,735

(22) PCT Filed: Sep. 30, 2020

(86) PCT No.: PCT/US2020/053429
§ 371 (c)(1),
(2) Date: Feb. 11, 2022

(87) PCT Pub. No.: WO2021/067370
PCT Pub. Date: Apr. 8, 2021

(65) Prior Publication Data
US 2022/0273947 A1     Sep. 1, 2022

Related U.S. Application Data

(60) Provisional application No. 62/908,567, filed on Sep. 30, 2019.

(51) Int. Cl.
*A61N 1/36*          (2006.01)
*A61N 1/04*          (2006.01)

(52) U.S. Cl.
CPC ....... *A61N 1/36034* (2017.08); *A61N 1/0456* (2013.01); *A61N 1/0492* (2013.01)

(58) Field of Classification Search
CPC .......................... A61N 1/36034; A61N 1/0456
USPC .......................................................... 607/72
See application file for complete search history.

(56) References Cited

U.S. PATENT DOCUMENTS

| | | | |
|---|---|---|---|
| 3,255,753 A | 6/1966 | Wing | |
| 3,388,699 A | 6/1968 | Webb et al. | |
| 3,620,219 A | 11/1971 | Barker | |
| 3,648,708 A | 3/1972 | Haeri | |
| 3,762,396 A | 10/1973 | Ballentine et al. | |
| 4,418,687 A | 12/1983 | Matsumoto et al. | |
| 4,431,000 A | 2/1984 | Butler et al. | |

(Continued)

FOREIGN PATENT DOCUMENTS

| | | |
|---|---|---|
| CN | 1204268 A | 1/1999 |
| CN | 1607970 A | 4/2005 |

(Continued)

OTHER PUBLICATIONS

Aston-Jones et al.; An integrative theory of locus coeruleus-norepinephrine function: adaptive gain and optimal performance; Annu. Rev. Neurosci.; 28: pp. 403-450; Jul. 21, 2005.

(Continued)

*Primary Examiner* — Nadia A Mahmood
(74) *Attorney, Agent, or Firm* — ShayGlenn LLP

(57)          ABSTRACT

Described herein are neuromodulator (e.g., neuromodulation apparatuses) that include an LED driver integrated circuit (IC) that is adapted to operate as a pulse generator for the neuromodulator.

19 Claims, 9 Drawing Sheets

(56)  References Cited

U.S. PATENT DOCUMENTS

| | | | |
|---|---|---|---|
| 4,541,432 A | 9/1985 | Molina-Negro et al. | |
| 4,646,744 A | 3/1987 | Capel | |
| 4,664,117 A | 5/1987 | Beck | |
| 4,865,048 A | 9/1989 | Eckerson | |
| 5,144,952 A | 9/1992 | Frachet et al. | |
| 5,183,041 A | 2/1993 | Toriu et al. | |
| 5,222,494 A | 6/1993 | Baker | |
| 5,335,657 A | 8/1994 | Terry et al. | |
| 5,342,410 A | 8/1994 | Braverman | |
| 5,397,338 A | 3/1995 | Grey et al. | |
| 5,476,481 A | 12/1995 | Schondorf | |
| 5,487,759 A | 1/1996 | Bastyr et al. | |
| 5,514,175 A | 5/1996 | Kim et al. | |
| 5,540,736 A | 7/1996 | Haimovich et al. | |
| 5,573,552 A | 11/1996 | Hansjurgens | |
| 5,578,065 A | 11/1996 | Hattori et al. | |
| 5,593,427 A | 1/1997 | Gliner et al. | |
| 5,738,647 A | 4/1998 | Bernhard et al. | |
| 5,792,067 A | 8/1998 | Karell | |
| 6,066,163 A | 5/2000 | John | |
| 6,280,454 B1 | 8/2001 | Wang | |
| 6,324,432 B1 | 11/2001 | Rigaux et al. | |
| 6,445,955 B1 | 9/2002 | Michelson et al. | |
| 6,463,328 B1 | 10/2002 | John | |
| 6,516,227 B1 | 2/2003 | Meadows et al. | |
| 6,526,318 B1 | 2/2003 | Ansarinia | |
| 6,567,702 B1 | 5/2003 | Nekhendzy et al. | |
| 6,731,987 B1 | 5/2004 | McAdams et al. | |
| 6,983,184 B2 | 1/2006 | Price | |
| 7,120,499 B2 | 10/2006 | Thrope et al. | |
| 7,146,217 B2 | 12/2006 | Firlik et al. | |
| 7,263,501 B2 | 8/2007 | Tirinato et al. | |
| 7,376,467 B2 | 5/2008 | Thrope et al. | |
| 7,422,555 B2 | 9/2008 | Zabara | |
| 7,577,481 B2 | 8/2009 | Firlik et al. | |
| 7,660,636 B2 | 2/2010 | Castel et al. | |
| 7,801,600 B1 | 9/2010 | Carbunaru et al. | |
| 7,891,615 B2 | 2/2011 | Bevirt | |
| 7,949,403 B2 | 5/2011 | Palermo et al. | |
| 8,029,431 B2 | 10/2011 | Tononi | |
| 8,034,294 B1 | 10/2011 | Goldberg | |
| 8,086,318 B2 | 12/2011 | Strother et al. | |
| 8,097,926 B2 | 1/2012 | De Graff et al. | |
| 8,116,875 B2 | 2/2012 | Osypka et al. | |
| 8,121,695 B2 | 2/2012 | Gliner et al. | |
| 8,150,537 B2 | 4/2012 | Tanaka et al. | |
| 8,190,248 B2 | 5/2012 | Besio et al. | |
| 8,197,276 B2 | 6/2012 | Egloff et al. | |
| 8,204,601 B2 | 6/2012 | Moyer et al. | |
| 8,239,030 B1 | 8/2012 | Hagedorn et al. | |
| 8,265,761 B2 | 9/2012 | Siever | |
| 8,280,502 B2 | 10/2012 | Hargrove et al. | |
| 8,346,337 B2 | 1/2013 | Heller et al. | |
| 8,380,315 B2 | 2/2013 | DeGiorgio et al. | |
| 8,428,738 B2 | 4/2013 | Valencia | |
| 8,463,383 B2 | 6/2013 | Sakai et al. | |
| 8,494,625 B2 | 7/2013 | Hargrove | |
| 8,494,627 B2 | 7/2013 | Bikson et al. | |
| 8,506,469 B2 | 8/2013 | Dietrich et al. | |
| 8,532,758 B2 | 9/2013 | Silverstone | |
| 8,560,075 B2 | 10/2013 | Covalin | |
| 8,571,651 B2 | 10/2013 | Ben-Ezra et al. | |
| 8,583,238 B1 | 11/2013 | Heldman et al. | |
| 8,583,256 B2 | 11/2013 | Tracey et al. | |
| 8,612,005 B2 | 12/2013 | Rezai et al. | |
| 8,639,343 B2 | 1/2014 | De Vos | |
| 8,660,644 B2 | 2/2014 | Jaax et al. | |
| 8,688,239 B2 | 4/2014 | Hartlep et al. | |
| 8,843,210 B2 | 9/2014 | Simon et al. | |
| 8,874,219 B2 | 10/2014 | Trier et al. | |
| 8,903,494 B2 | 12/2014 | Goldwasser et al. | |
| 8,983,621 B2 | 3/2015 | Hou et al. | |
| 9,002,458 B2 | 4/2015 | Pal et al. | |
| 9,014,811 B2 | 4/2015 | Pal et al. | |
| 9,067,054 B2 | 6/2015 | Simon et al. | |
| 9,168,374 B2 | 10/2015 | Su | |
| 9,205,258 B2 | 12/2015 | Simon et al. | |
| 9,233,244 B2 | 1/2016 | Pal et al. | |
| 9,248,292 B2 | 2/2016 | Trier et al. | |
| 9,333,334 B2 | 5/2016 | Jeffery et al. | |
| 9,364,674 B2 | 6/2016 | Cook et al. | |
| 9,393,401 B2 | 7/2016 | Goldwasser et al. | |
| 9,393,430 B2 | 7/2016 | Demers et al. | |
| 9,399,126 B2 | 7/2016 | Pal et al. | |
| 9,415,219 B2 | 8/2016 | Simon et al. | |
| 9,440,070 B2 | 9/2016 | Goldwasser et al. | |
| 9,446,242 B2 | 9/2016 | Griffith | |
| 9,474,891 B2 | 10/2016 | Demers et al. | |
| 9,474,905 B2 | 10/2016 | Doan et al. | |
| 9,517,351 B2 | 12/2016 | Charlesworth et al. | |
| 9,655,772 B2 | 5/2017 | Smith et al. | |
| 9,656,076 B2 | 5/2017 | Trier et al. | |
| 9,700,725 B2 | 7/2017 | Zhu | |
| 9,731,116 B2 | 8/2017 | Chen | |
| 9,744,347 B2 | 8/2017 | Chen et al. | |
| 9,764,133 B2 | 9/2017 | Thomas et al. | |
| 9,782,587 B2 | 10/2017 | Trier et al. | |
| 9,956,405 B2 | 5/2018 | Goldwasser et al. | |
| 9,968,780 B2 | 5/2018 | Pal et al. | |
| 10,258,788 B2 | 4/2019 | Jeffery | |
| 10,293,161 B2 | 5/2019 | Charlesworth et al. | |
| 10,426,945 B2 | 10/2019 | Tyler et al. | |
| 10,485,972 B2 | 11/2019 | Pal et al. | |
| 10,537,703 B2 | 1/2020 | Tyler et al. | |
| 10,646,708 B2 | 5/2020 | Goldwasser et al. | |
| 10,814,131 B2 | 10/2020 | Goldwasser et al. | |
| 11,033,731 B2 | 6/2021 | Jeffery et al. | |
| 11,235,148 B2 | 2/2022 | Charlesworth et al. | |
| 2001/0000187 A1 | 4/2001 | Peckham et al. | |
| 2002/0116036 A1 | 8/2002 | Daignault et al. | |
| 2003/0088279 A1 | 5/2003 | Rissmann et al. | |
| 2003/0134545 A1 | 7/2003 | McAdams et al. | |
| 2003/0171685 A1 | 9/2003 | Lesser et al. | |
| 2003/0225323 A1 | 12/2003 | Kiani et al. | |
| 2004/0019370 A1 | 1/2004 | Gliner et al. | |
| 2004/0098065 A1 | 5/2004 | Hagglof et al. | |
| 2004/0158305 A1 | 8/2004 | Axelgaard | |
| 2004/0267333 A1 | 12/2004 | Kronberg | |
| 2005/0165460 A1 | 7/2005 | Erfan | |
| 2005/0267388 A1 | 12/2005 | Hanna | |
| 2005/0283259 A1 | 12/2005 | Wolpow | |
| 2006/0047215 A1 | 3/2006 | Newman et al. | |
| 2006/0064139 A1 | 3/2006 | Chung et al. | |
| 2006/0149119 A1 | 7/2006 | Wang | |
| 2006/0190057 A1 | 8/2006 | Reese | |
| 2006/0195159 A1 | 8/2006 | Bradley et al. | |
| 2006/0206163 A1 | 9/2006 | Wahlstrand et al. | |
| 2006/0247985 A1 | 11/2006 | Liamos et al. | |
| 2007/0053466 A1 | 3/2007 | Klostermann | |
| 2007/0088419 A1 | 4/2007 | Fiorina et al. | |
| 2007/0097593 A1 | 5/2007 | Armstrong | |
| 2007/0100275 A1 | 5/2007 | Fischer et al. | |
| 2007/0173890 A1 | 7/2007 | Armstrong | |
| 2007/0213790 A1 | 9/2007 | Nolan et al. | |
| 2007/0276451 A1 | 11/2007 | Rigaux | |
| 2008/0015641 A1 | 1/2008 | Armstrong et al. | |
| 2008/0045882 A1 | 2/2008 | Finsterwald | |
| 2008/0071626 A1 | 3/2008 | Hill | |
| 2008/0097564 A1 | 4/2008 | Lathrop | |
| 2008/0132974 A1 | 6/2008 | Strother et al. | |
| 2008/0207985 A1 | 8/2008 | Farone | |
| 2008/0208266 A1 | 8/2008 | Lesser et al. | |
| 2008/0215113 A1 | 9/2008 | Pawlowicz | |
| 2008/0275293 A1 | 11/2008 | Lattner et al. | |
| 2008/0281368 A1 | 11/2008 | Bulkes et al. | |
| 2008/0319505 A1 | 12/2008 | Boyden et al. | |
| 2009/0048642 A1 | 2/2009 | Goroszeniuk | |
| 2009/0054952 A1 | 2/2009 | Glukhovsky et al. | |
| 2009/0076559 A1 | 3/2009 | Libbus et al. | |
| 2009/0099623 A1 | 4/2009 | Bentwich | |
| 2009/0112280 A1 | 4/2009 | Wingeier et al. | |
| 2009/0177243 A1 | 7/2009 | Lebedev et al. | |
| 2009/0210028 A1 | 8/2009 | Rigaux et al. | |
| 2009/0240303 A1 | 9/2009 | Wahlstrand et al. | |

(56) References Cited

U.S. PATENT DOCUMENTS

| | | |
|---|---|---|
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0145428 A1 | 6/2010 | Cameron et al. |
| 2010/0152817 A1 | 6/2010 | Gillbe |
| 2010/0222734 A1 | 9/2010 | Jayes et al. |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1 | 2/2011 | Hacking et al. |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1 | 12/2011 | Hargrove |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1 | 7/2012 | Simon et al. |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0155561 A1 | 6/2013 | Chein-Feng |
| 2013/0158627 A1 | 6/2013 | Gozani et al. |
| 2013/0184779 A1 | 7/2013 | Bikson et al. |
| 2013/0204315 A1 | 8/2013 | Wongsampigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |
| 2014/0309709 A1 | 10/2014 | Gozani et al. |
| 2014/0324138 A1* | 10/2014 | Wentz .................. A61N 5/0622 607/90 |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0335877 A1 | 11/2015 | Jeffery et al. |
| 2015/0360038 A1 | 12/2015 | Zottola et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2017/0076414 A1 | 3/2017 | Egnal et al. |
| 2017/0290546 A1 | 10/2017 | Antonio et al. |
| 2018/0036533 A1 | 2/2018 | Yoo et al. |
| 2019/0321636 A1 | 10/2019 | Law et al. |
| 2020/0147340 A1 | 5/2020 | Tyler et al. |
| 2020/0155790 A9 | 5/2020 | Tyler et al. |
| 2020/0297999 A1 | 9/2020 | Pal |
| 2022/0152389 A1 | 5/2022 | Charlesworth et al. |
| 2022/0203092 A1 | 6/2022 | Law et al. |
| 2024/0058606 A1 | 2/2024 | Law et al. |
| 2025/0108215 A1 | 4/2025 | Charlesworth et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 06339531 A | 12/1994 |
| JP | 10108913 A | 4/1998 |
| JP | 2001129100 A | 5/2001 |
| JP | 2001293097 A | 10/2001 |
| JP | 2002306604 A | 10/2002 |
| JP | 200310230 A | 1/2003 |
| JP | 2006192302 A | 7/2006 |
| JP | 3129187 U | 1/2007 |
| JP | 2007535372 A | 12/2007 |
| JP | 200985901 A | 4/2009 |
| JP | 2009513248 A | 4/2009 |
| JP | 2011118293 A | 6/2011 |
| JP | 2011519654 A | 7/2011 |
| JP | 2013512076 A | 4/2013 |
| WO | WO90/09810 A1 | 9/1990 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/018120 A1 | 3/2003 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |

(56) References Cited

FOREIGN PATENT DOCUMENTS

| | | | |
|---|---|---|---|
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/022215 A1 | 2/2014 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/201525 A1 | 11/2017 |
| WO | WO2019/138407 A1 | 7/2019 |

OTHER PUBLICATIONS

Aston-Jones et al.; Role of locus coeruleus in attention and behavioral flexibility; Biological Psychiatry; 46(9); pp. 1309-1320; Nov. 1, 1999.

Axelgaard Manufacturing Co. Ltd.; Little PALS® (product information); 2 pgs.; printed Feb. 11, 2013 from http://www.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Chaieb et al.; Transcranial alternating current stimulation in the low kHz range increases motor cortex excitability; Restor Neurol Neurosci; 29(3); pp. 167-175; Mar. 2011.

Cook et al.; Trigeminal nerve stimulation in major depressive disorder: acute outcomes in an open pilot study; Epilepsy and Behavior; 28(2): pp. 221-226; Aug. 31, 2013.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Degiorgio et al., Trigeminal nerve stimulation for epilepsy: long-term feasibility and efficacy; Neurology; 72(10): pp. 936-938; Mar. 10, 2009.

Degiorgio et al.; Randomized controlled trial of trigeminal nerve stimulation for drug-resistant epilepsy; Neurology; 80(9); pp. 786-791; Feb. 26, 2013.

Digitimer Ltd.; DS2 and DS3 Isolated Stimulator (product information); 2 pgs.; downloaded from http://www.digitimer.com/research/stimulators/index.htm on Feb. 10, 2014.

Elder et al.; The cortisol awakening response—applications and implications for sleep medicine; Sleep Medicine Reviews; 18(3): pp. 215-224; Jun. 30, 2014.

Electozyme; Company and Product Information; 3 pgs.; printed Feb. 11, 2014 from http://electrozyme.com/applications/.

Eschenko et al.; Noradrenergic neurons of the locus coeruleus are phase locked to cortical up-down states during sleep; Cerebral Cortex; 22(2); pp. 426-435; Feb. 1, 2012.

Feurra et al.; Frequency specific modulation of human somatosensory cortex; Front Psychol; 2(13); 6 pgs.; Feb. 2011.

Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.

Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.

GoFlow; tDCS Kit; product information; 9 pgs..; printed Feb. 10, 2014 (http://flowstateengaged.com/).

Golestanirad et al; Analysis of fractal electrodes for efficient neural stimulation; Frontiers in Neurengineering; 6(3); 10 pages; Jul. 2013.

Gracenote; Timeline-metadata-api; 3 pages; retrieved from the internet Jul. 7, 2015; (https://github.com/gracenote/timeline-metadata-api/blob/master/README.md).

Granger et al.; Salivary alpha-amylase in biobehavioral research: recent developments and applications; Annals of the New York Academy of Sciences; 1098(1); pp. 122-144; Mar. 1, 2007.

Grindhouse Wetware; Thinking Cap; product information; 1 pg.; printed Feb. 10, 2014 (http://www.grindhousewetware.com/thinkingcap.html).

Gummadavelli et al.; Neurostimulation to improve level of consciousness in patients with epilepsy. Neurosurgical Focus; 38(6); pp. E10; (manuscript version, 14 pages); Jun. 2015.

Hajos et al.; Norepinephrine but not serotonin reuptake inhibitors enhance theta and gamma activity of the septo-hippocampal system; Neuropsychopharmacology; 28(5); pp. 857-864; May 1, 2003.

Hass et al.; Waking with the hypothalamus. Pflugers Arch R Eur. J. Physiol.; 463(1): pp. 31-42; Jan. 1, 2012.

Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.

Hirotsu et al.; Interactions between sleep, stress, and metabolism; From physiological to pathological conditions; Sleep Science; 8(3); pp. 143-152; Nov. 2015.

Horvath et al.; Evidence that transcranial direct current stimulation (tDCS) generates little-to-no reliable neurophysiologic effect beyond MEP amplitude modulation in healthy human subjects: A systematic review; Neuropsychologia: 66: pp. 213-236; Jan. 31, 2015.

Just et al.; Bold responses to trigeminal nerve stimulation; Magnetic Resonance Imaging; 28(8): pp. 1143-1151; Oct. 31, 2010.

(56)         References Cited

OTHER PUBLICATIONS

Kanai et al.; Frequency-dependent electrical stimulation of the visual cortex; Curr. Biol.; 18(23); pp. 1839-1843; Dec. 9, 2008.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441(7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population, The Journal of Headache and Pain, 14(1); p. 95; (manuscript version, 8 pages) Dec. 1, 2013.
Mcgough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Paulus, W.; Transcranial electrical stimulation (tES-tDCS; (RNS, tACS) methods; Neuropsychol Rehabil.; 21(5); pp. 602-617; Oct. 2011.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Prausnitz; The effects of electric current applied to skin: a review for transdermal drug delivery; Advanced Drug Delivery Reviews; vol. 18; pp. 395-425; Feb. 8, 1996.
Pusch et al.; Electrical stimulation of the vestibular system prevents postoperative nausea and vomiting: Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Saiote et al.; High-frequency TRNS reduces BOLD activity during visuomotor learning; PLOS one; 8(3); e59669; 8 pgs.; Mar. 2013.
Sara; The locus coeruleus and noradrenergic modulation of cognition; Nature Reviews Neuroscience; 10(3): pp. 211-223. Mar. 1, 2009.

Schmidt et al.; Adrenaline rush: the role of adrenergic receptors in stimulant-induced behaviors; Molecular Pharmacology; 85(4): pp. 640-650; Apr. 1, 2014.
Schutter et al.; Brain oscillations and frequency-dependent modulation of cortical excitability; Brain Stimulation; 4(2); pp. 97-103; Apr. 2011.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking. Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.
STD Pharmaceutical Products; Idrostar intophoresis machine (product and use information); 9 pgs.; Dec. 2011 (printed Feb. 11, 2014 from http://www.iontophoresis.info/instructions/).
Strassman et al; Response of brainstem trigeminal neurons to electrical stimulation of the dura; Brain Research; 379(2): pp. 242-250; Aug. 6, 1986.
Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.
Terney et al.; Increasing human brain excitability by transcranial high-frequency random noise stimulation; The Journal of Neuroscience; 28(52); pp. 14127-14155; Dec. 2008.
Thoma et al.; Acute stress responses in salivary alpha-amylase predict increases of plasma norepinephrine; Biological Psychology; 91(3): pp. 342-348; Dec. 31, 2012.
Tremblay et al.; Uncertain Outcome of Prefrontal tDCS; Brain Stimulation; 7(6): pp. 773-783; Dec. 31, 2014.
Trevizol et al.; Trigeminal Nerve Stimulation (TNS) for Generalized Anxiety Disorder: A Case Study; Brain Stimulation; 8(3): pp. 659-660; January, 1, 2015.
Trevizol et al.; Trigeminal Nerve Stimulation (TNS) for Post-traumatic Stress Disorder: A Case Study; Brain Stimulation; 8(3): pp. 676-678; Jan. 1, 2015.
Turi et al.; Both the cutaneous sensation and phosphene perception are modulated in a frequency-specific manner during transcranial alternating current stimulation; Restor. Neurol. Neurosci.; 31(3); pp. 275-285; Jan. 2013.
Tyler et al.; Transdermal neuromodulation of noradrenergic activity suppresses psychophysiological and biochemical stress responses in humans; Scientific Reports; 5; (manual transcript, 22 pages); Feb. 8, 2015.
Tyler et al.; U.S. Appl. No. 61/550,334 entitled "Improvement Of Direct Communication," filed Oct. 21, 2011.
Tyler et al.; U.S. Appl. No. 61/663,409 entitled "Device And Methods For Noninvasive Neuromodulation Using Targeted Transcranial Electrical Stimulation," filed Jun. 22, 2012.
Tyler et al.; U.S. Appl. No. 62/166,674 entitled "Systems And Methods For Suppression Of Stress Responses By Transdermal Electrical Neuromodulation," filed May 26, 2015.
Upadhyay et al.; Noninvasive mapping of human trigeminal brainstem pathways; Magnetic Resonance in Medicine; 60(5): pp. 1037-1046; Nov. 1, 2008.
Van Stegeren et al.; Salivary alpha amylase as marker for adrenergic activity during stress: effect of betablockade; Psychoneuroendocrinology; 31(1); pp. 137-141; Jan. 31, 2006.
Voisin et al.; Nociceptive stimulation activates locus coeruleus neurones projecting to the somatosensory thalamus in the rat; The Journal of Physiology; 566( 3); pp. 929-937; Aug. 1, 2005.
Voss et al.; Induction of self awareness in dreams through frontal low current stimulation of gamma activity; Nature Neuroscience; 17(6); pp. 810-812; Jun. 1, 2014.
Watson et al.; Development and validation of brief measures of positive and negative affect: the PANAS scales; Jouranl of Personality and Social Psychology; 54(6); pp. 1063-1070; Jun. 1988.
Weiss et al; Validity of Activity-Based Devices to Estimate Sleep; Journal of Clinical Sleep Medicine : 6(4); pp. 336-342; Aug. 2010.

(56)     References Cited

OTHER PUBLICATIONS

Pal et al.; U.S. Appl. No. 14/956,193 entitled "Transdermal electrical stimulation devices for modifying or inducing cognitive state," filed Dec. 1, 2015.

* cited by examiner

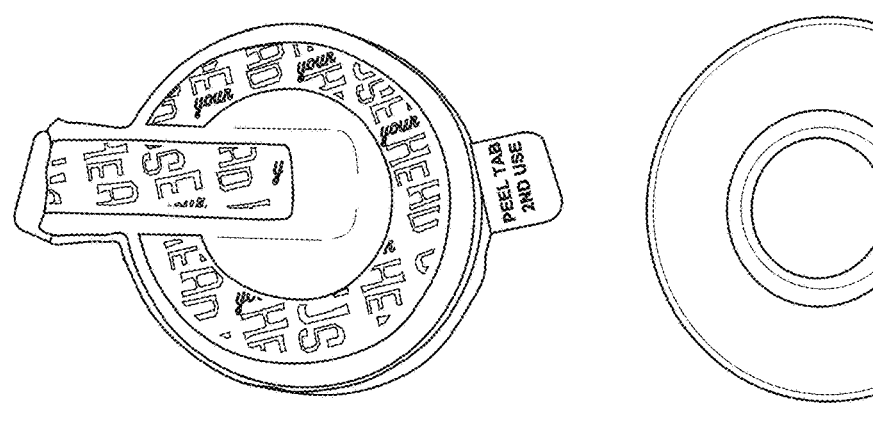
FIG. 1A                    FIG. 1B
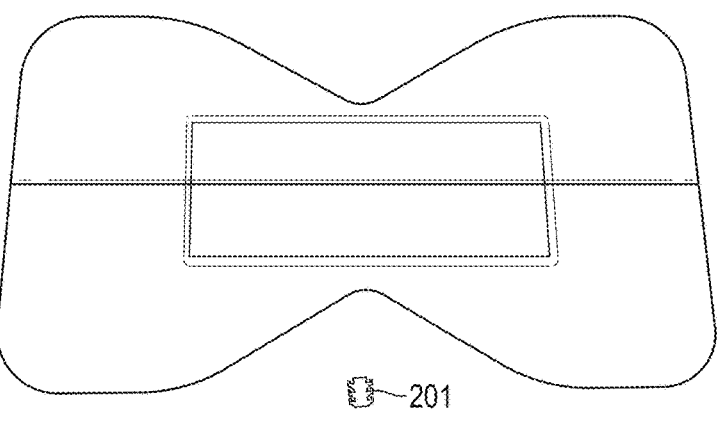
FIG. 2
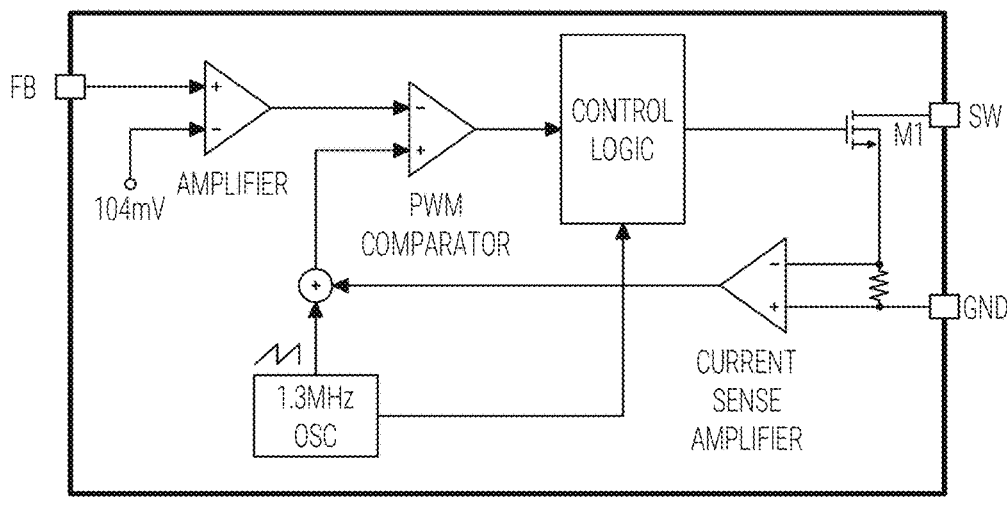
FIG. 3A

MODIFICATIONS TO LED DRIVER IC

SAMPLE OF OUTPUT CURRENT ADDED
TO N-PULSE TO SWITCH OFF THE LED
DRIVER PWM PULSES WHEN OUTPUT
HITS THE TARGET CURRENT

N-PULSE IS THE PULSE OUTPUT FROM
THE MICRO CONTROLLER. THE LED
DRIVER IC's OUTPUT IS SWITCHED ON
AND OFF ACCORDING TO THE INVERSE
OF THE N-PULSE SIGNAL

FEEDBACK INPUT TO CONTROL CURRENT.
NOTE AN INVERSE TO THE TENS WAVEFORM INJECTED
HERE WILL MODULATE THE OUTPUT CURRENT

NEUROMODULATOR APPARATUSES COMPRISING LED DRIVER INTEGRATED CIRCUITS

CROSS REFERENCE TO RELATED APPLICATIONS

This patent application claims priority to U.S. provisional patent application no. 62/908,567, titled "NEUROMODU-LATOR APPARATUSES COMPRISING LED DRIVER INTEGRATED CIRCUITS," filed on Sep. 30, 2019, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein neuromodulation apparatuses, including devices and systems, and methods of their use.

BACKGROUND

Neuromodulation, and particularly non-invasive neuro-modulation, can affect nerves and neuronal activity, and may have therapeutic effects and/or may be useful for modulating cognitive states, perception, and motor output. For example, transdermal electric stimulation ("TES") using skin, e.g., scalp, electrodes has been used to affect brain function and nervous system function in humans and includes transcranial alternating current stimulation ("tACS"), transcranial direct current stimulation ("tDCS"), cranial electrotherapy stimulation ("CES"), transcranial random noise stimulation ("tRNS"), trigeminal nerve stimulation ("TNS"), and vagal nerve stimulation ("VNS"), amongst other forms known to those skilled in the art.

TES has been used therapeutically in various clinical applications, including treatment of pain, depression, epilepsy, ADHD, and tinnitus. This neuromodulation has been demonstrated to lower physiological stress and anxiety, improve sleep, and has potential as a therapy for specific auto-immune disorders such as psoriasis. It has the potential to treat numerous neurogenic inflammatory conditions. Neuromodulation has been shown, for example, to result in increased energy and motivation. See, e.g., U.S. Pat. Nos. 9,014,811, 9,002,458, 9,233,244, 9,399,126 and 9,333,334. The effect is comparable to caffeine or energy drinks available in the market today, though the effect can be stronger in certain individuals.

Despite the research to date on TES neuromodulation, existing systems and methods for delivering TES are lacking. In particular, miniaturized systems that incorporate hardware components with a low profile, comfortable, and/or familiar form factor for convenient, intuitive, easy to use, comfortable, and on-the-go TES free from cumbersome electrical wires, have been lacking.

SUMMARY OF THE DISCLOSURE

Described herein are neuromodulator (e.g., neuromodulation apparatuses) that typically include an LED driver integrated circuit (IC) that is adapted to operate as a pulse generator for the neuromodulator. Although the LED driver IC (also referred to as an LED driver chip or an LED driver) is designed to drive a string of LEDS, the apparatuses (e.g., devices, systems, etc., including neuromodulators) described herein instead have adapted the LED driver IC to operate as safe and effective pulse generators as part of a neuromodulator, in conjunction with two or more electrodes, a microcontroller and circuitry for adjusting the function of the intact LED driver IC.

Traditionally, neural modulation has required a sophisticated constant current waveform that may be pulsed at variable intervals and with scheduled changes in pulse on time and pulse amplitudes to keep the neurons from adapting to the modulation signal. These requirements made the electronics expensive. Therefore it is expensive and impractical to provide disposable devices, despite the fact that the skin coupling gel contaminated by skin oil loses adhesion after one or two uses.

Described herein are methods of using an existing LED chip that is configured specifically for controlling LED lights and is readily available at low cost, so that it can be used to act as a pulse generator appropriate for transdermal neural electrical stimulation. High-volume, commercial LED driver integrated circuits (ICs) are readily available. These chips are designed for an entirely different application; specifically, they are designed to act as LED drivers for driving 8 to 10 LEDs (light emitting diodes) in series. These IC operate by converting a low voltage from a single battery to a range of 20 volts to 30 volts, and are used in quantities of approximately 100s of millions a year in inexpensive flash lights, or in virtually any device (e.g., hand held devices) with displays that require LED back-lighting.

Examples of such LED driver chips may include, e.g., PT4110 (PowTech), R1208 Series PWM Step-up DCDC converter for White LED (RICOH), LT3497 (Linear Technology), CAT4137 (ON Semiconductor), etc. In general an LED driver chip includes an oscillator having an operating frequency between 1 MHz to 2 MHz configured to drive a switch at the operating frequency, an error amplifier that reads a feedback voltage to control on time and off time of the switch, a current sense amplifier that reads the current passing through the switch to keep the current from going beyond the capability of the switch, and control logic.

In some variations the systems and methods described herein may include one or more LED driver chips with additional circuitry to provide 20 volts, 1 MHz AC, pulse-modulated RF output, where the pulse modulation control may be provided by an external micro-controller.

In some variations the LED drive IC does not provide a high enough voltage for neural modulation, which typically requires voltage in a range of about 40 volts to 60 volts. In some variation described herein a voltage doubler circuit or voltage tripler circuit using several diodes and capacitors can further multiply the voltage into a range needed for neural modulation. Normally a voltage doubler or voltage tripler circuits requires bulky capacitors; as described herein, by using an LED driver running at very high frequencies (e.g., 1 MHz and above), the size of the capacitors used may be become small enough for surface mount printed circuits. Further, these LED driver may be modified by providing circuitry to modulate the pulse amplitude, pulse duration, and/or pulse frequency. Thus, the micro-controller does not need to operate at high frequency (e.g., at 1 MHz and above); instead the high-frequency operation is provided by the LED driver chip. The LED drivers described herein typically have a dimming control function configured to modulate the brightness of the LED light. This control pin, in some LED driver chips, can respond fast enough to pulses typical of neural modulation, such as in the range of 50 microsecond to 200 microseconds.

In any of the embodiments described herein, the voltage multiplier (e.g., voltage doubler, voltage tripper) may be optional, as 20-25 volts may be sufficient to drive neuro-modulation, and the LED driver IC may be sufficient to provide this voltage without requiring additional voltage multiplier circuitry.

Constant current output may be achieved using the LED driver chips to provide effective neural modulation. The signal may be delivered at a constant current during the pulse on time. An LED driver chip may have a feedback pin to shut off the step-up transistors. In some variation a resistor in series with the neural modulation path may be used; by sensing the voltage drop on the series resistor, and feeding that voltage to the feedback pin, the apparatus can shut off the voltage step up function when the output electrical current for neural modulation reaches a target value. Thus constant current may therefore be achieved by rapidly switching the step-up transistor on and off around the target value.

In any of these methods and apparatuses described herein, user safety may be enhanced by limiting the maximum voltage applied to the skin. Most LED driver chips may keep pumping up the voltage until a target current is reached. In the case of a high impedance load, the chip can get to such a high voltage that a system shut down occurs. Thus, in some variations described herein, a Zener diode, which starts conducing at the maximum target voltage of around 62 volts to 65 volts, may be used. The Zener diode also prevents the chip from shutting down during the period when the elec-trode (e.g., a gel patch) is in the air, before application to the skin. Likewise the diode prevents shutdown when the gel patch falls off skin accidentally.

Any of these methods and apparatuses may provide skin re-attachment detection. For example, for ease of use, an apparatus including a gel patch should initiate neural modu-lation only when attached to skin. This can be achieved using Analog-to-Digital conversion. Alternately, as described herein, the Zener diode's conduction may signify the gel patch being off the skin, e.g., in the air. At that time, the pulse duration applied to the gel patch may be drastically reduced, for user safety and comfort. This reduced duration pulse may now acts as a skin detection pulse, to determine if, e.g., when, the patch is re-applied to skin. When this detection pulse goes further down in amplitude (as detected by a second Zener diode, or by an A/D converter in the micro-controller), the circuit may increase the pulse duration back to normal.

Constant voltage output may be achieved by switching the feedback control from sensing electrical current to the sensing of electrical output voltage. This mode switch may be achieved by a simple, low cost, transistor. A resistor ladder may be used to drop the output voltage to the typically lower voltage of the sensing input.

Any of the apparatuses described herein may include over-current protection. The inexpensive chip may include built-in over current protection cycle by cycle. This over-current shut down protection may help to protect the user in case the chip runs at a spurious mode that consumes a lot of current. Alternatively or additionally, an apparatus include the adapted LED driver IC may be configured to provide thermal shut down. For example, in the case that the chip draws a lot of power in a spurious mode, the chip may heat up (e.g., typically at around 200 milliwatts) and may trigger a thermal shut down. This feature may also be useful for user protection.

In some variations, charge accumulated on the skin may be discharged after each neural-modulation pulse, e.g., by a turning on a simple transistor, by the micro-controller, upon the completion of each neural modulation pulse. Thus, a complete neural-modulation circuit can be achieved, e.g., by combining an LED driver IC with the above circuit com-ponents, e.g., a voltage multiplier (such as a voltage doubler or voltage tripler), which may be optional, a feedback circuit sensing voltage drop in the neural modulation path (and feeding back to a feedback pin to shut off the step-up transistors in the LED driver), a skin discharge circuit, and/or a Zener diode to limit the maximum voltage applied to the skin. In some variations, these circuits may generate 20 Volts, pulse modulated (e.g., 1 MHz AC). Thus, these circuit assemblies may be used for TENS devices, including for pain control and physical therapy, and may provide low-cost and reliable and highly compact, including dispos-able or limited-use, pulse generators that are highly flexible, easier to dispense, and more convenient to the user than traditional pulse generators, even as compared to dedicated integrated circuit pulse generators.

For example, described herein are neuromodulator appa-ratuses that may include: an electrode pair (e.g., a first electrode and a second electrode); a microcontroller storing one or more neural modulation waveform parameters; and an LED driver integrated circuit (IC) adapted to function as a pulse generator, wherein a first pin of the LED driver IC is in electrically communication with a first electrode of the electrode pair, and a feedback pin on the LED driver IC is coupled to the microcontroller to modulate an output of the LED driver IC on the first pin in accordance to the one or more neural modulation waveform parameters stored in the microcontroller; wherein the output from the LED driver integrated circuit is modulated by the microcontroller and output by the first electrode.

Any of these apparatuses may include a voltage multiplier circuit (e.g., voltage doubler, voltage tripler, etc.) in electri-cal communication with the first pin and the first electrode so that the voltage multiplier circuit multiplies the voltage output of the LED driver IC delivered before the first electrode. For example, the voltage multiplier circuit may be configured to multiple the voltage from the LED driver IC to greater than 50 V.

The LED driver integrated circuit comprises an oscillator having an operating frequency between 1 MHz to 2 MHz that is configured to drive a switch at the operating fre-quency. The LED driver IC may also include an error amplifier that reads a feedback voltage to control on time and off time of the switch, a current sense amplifier that reads the current passing through the switch to keep the current from going beyond the capability of the switch, and control logic. In some variations the switch may be inte-grated as part of the LED driver IC; in some variations the switch may be external.

The electrode pair may comprise a pair of hydrogel skin contacts. These contacts may be concentric. In some varia-tions, described below, the apparatus may include multiple layers of hydrogel so that an outer layer (or layers) may be removed to expose a clean lower layer, allowing the appa-ratus to be reused.

Any of these apparatuses may include an OR gate on the feedback pin of the LED driver IC. The OR gate may receive input from the microcontroller and from a sample input that is in electrical communication with the first electrode. This OR gate may therefore operate as a logical OR gate.

In general, the apparatuses described herein may be configured so that the LED driver IC may operate with a skin discharge circuitry that is in electrical communication with the microcontroller, and may be configured to discharge capacitive energy from skin during or after neuromodulation is applied to the skin. In any of the apparatuses described herein a skin detection circuit may be included and may be coupled to a pin on the LED driver IC, wherein the skin sensing circuit is configured to detect contact with skin based on an output voltage of the LED driver IC. For example, the skin detection circuit may be is configured to trigger a signal to the microcontroller to switch output pulses from the LED driver IC to a short duration, low-voltage pinging pulses when the voltage from the LED driver IC exceeds a threshold. The skin detection circuit may be further configured to detect contact with the skin when the voltage of the pinging pulses falls below a threshold voltage.

Any of these apparatuses may include a low pass filter in electrical communication with an OVP pin of the LED driver IC, wherein the apparatus is configured to shut down the LED driver when a DC is detected. This may protect the subject wearing the apparatus from electrical harm.

In some variations the LED driver IC applies an output pulse (pulse generator output) that is inverted compared to what is input by the microcontroller. Thus, the microcontroller may be configured to store an inverse of a neural modulation wave sequence that is between 0 mV and 100 mV, for application to the feedback pin of the LED driver IC. Thus, the microcontroller may be adapted to provide the LED driver IC with the necessary waveforms.

In any of the apparatuses described herein, the electrodes may include a conductive adhesive film that electrically coupling a gel electrode pad(s) to the output from the configured LED driver IC (e.g., the output of the first pin of the LED driver IC).

In general, unlike the typical output of an LED driver IC, when driving a string or chain of LEDs, may be an AC output. Thus, the associated circuitry, including the microcontroller and the other feedback inputs to the LED driver IC, may modulate the output of the LED driver to be an AC output.

In any of the apparatuses described herein, the LED driver IC may further include an enable pin in electrical communication with the microcontroller, wherein the apparatus is configured to modulate the enable pin when a neuromodulation frequency is between about 0.1 HZ to 100 HZ A neuromodulator apparatus may include: an electrode pair comprising a first electrode and a second electrode; a microcontroller storing one or more neural modulation waveform parameters (which may be inverted); and an LED driver integrated circuit (IC) adapted to function as a pulse generator, wherein a first pin of the LED driver IC is configured to output the pulsed signal for driving neuromodulation (and may be in electrical communication, either direct or indirect) with the electrode pair, and a feedback pin on the LED driver IC is coupled to the microcontroller to modulate an output of the LED driver IC on the first pin in accordance to the one or more neural modulation waveform parameters stored in the microcontroller, wherein the one or more neural modulation waveforms are inverted and normalized to between 0 mV and 100 mV, so that output from the LED driver IC is modulated by the microcontroller and output by the first electrode.

In some variations the LED driver IC is coupled to a voltage multiplier circuit. For example, a neuromodulator apparatus may include: an electrode pair comprising a first electrode and a second electrode; a voltage multiplier circuit in electrical communication with the first electrode configured to provide a peak output voltage of 50 V or greater; a microcontroller storing one or more neural modulation waveform parameters; and an LED driver integrated circuit (IC) adapted to function as a pulse generator, wherein a first pin of the LED driver IC is coupled to the voltage multiplier circuit and a feedback pin on the LED driver IC is coupled to the microcontroller to modulate an output of the LED driver IC on the first pin in accordance to the one or more neural modulation waveform parameters stored in the microcontroller, wherein the one or more neural modulation waveforms are inverted and normalized to between 0 mV and 100 mV; wherein the first electrode is in electrical communication with the voltage multiplier circuit so that output from the LED driver IC is modulated by the microcontroller, amplified by the voltage multiplier circuit and output by the first electrode.

A neuromodulator apparatus may comprise: a pair of hydrogel electrodes; a microcontroller storing one or more neuromodulation waveform parameters; and an LED driver integrated circuit (IC) comprising a first pin, a feedback pin, an over-voltage protection pin, and an enable (EN) pin, wherein an input to the hydrogel electrodes is in electrical communication with the first pin, further wherein both the microcontroller and a feedback in electrical communication with the input to the hydrogel electrodes are in electrical communication with the feedback pin; so that the LED driver integrated circuit may operate as a pulse generator providing neuromodulation output to the pair of hydrogel electrodes.

For example, a neuromodulator apparatus may comprise: a pair of hydrogel electrodes; a voltage multiplier circuit having an output in communication with one or more of the hydrogel electrodes; and a microcontroller storing one or more neuromodulation waveform parameters; an LED driver integrated circuit (IC) comprising a first pin, a feedback pin, an over-voltage protection pin, and an enable (EN) pin, wherein an input to the voltage multiplier circuit is in electrical communication with the first pin, further wherein both the microcontroller and the output of the voltage multiplier circuit are in electrical communication with the feedback pin; wherein the LED driver integrated circuit is configured to operate as a pulse generator providing neuromodulation output to the pair of hydrogel electrodes.

The microcontroller and the output of the feedback in electrical communication with the input to the hydrogel electrodes (in some variations, the voltage multiplier circuit) are connected to the feedback pin through an OR gate.

As mentioned, any of these apparatuses may include a skin detection circuit coupled to the EN pin and configured to put the LED driver IC to sleep when one or more of the pair of hydrogel electrodes are removed from the skin. The one or more neuromodulation waveforms parameters may be between 0 and 100 mV and are inverted compared to an output of the LED driver IC.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A and 1B shows front and back views, respectively of an example of a neuromodulation apparatus, configured as a patch, that may include an LED driver IC adapted to function as the pulse generator, as described herein.

FIG. 2 shows an example of an LED driver IC next to a Band-Aid for scale.

FIG. 3A is one example of a block diagram illustrating one example of an LED driver IC that may be used in any of the apparatuses described herein.

DETAILED DESCRIPTION

Figure 3B:
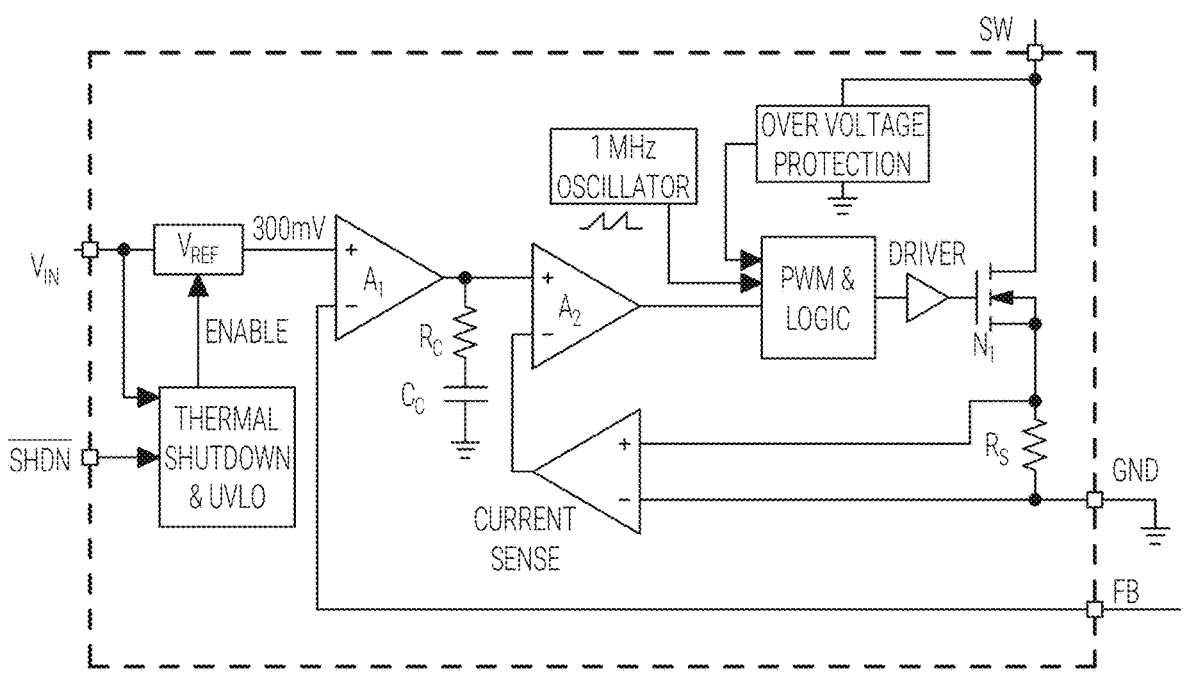
FIG. 3B is an example of a block diagram illustrating one example of an LED driver IC that may be used in any of the apparatuses described herein.

Described herein are low-cost and reliable pulse generators that adapt existing integrated circuit LED drivers (e.g., step-up DC/DC LED driver integrated circuits) with a feedback circuit sensing voltage drop in the neural modulation path (and feeding back to a feedback pin to shut off the step-up transistors in the LED driver), a skin discharge circuit, and/or a Zener diode to limit the maximum voltage applied to the skin. In some variations, the apparatuses may also include a voltage multiplier (such as a voltage doubler or voltage tripler) circuit. These pulse generators are particularly well suited for use as external neural modulator or TENS devices, and in particular devices include one or more gel electrodes for attaching to the skin.

For example, neural modulation and TENS may both used electrically conductive gel to couple a small electric current into skin to generate an electric field of short time-duration pulses around neural fiber bundles. In order to overcome the high resistance of the skin, the voltage may be fairly high for the pulses, e.g., on the order of 40 Volts to 100 volts. For optimal effects, the treatment pulses may be constant current during the time it was turned on. Traditionally this has required a complicated (and correspondingly expensive) customized pulse generator and microcontroller circuitry. Further, because the gel forming the electrode may get dirty after attaching to skin and may need to be replaced after a few uses, it would be preferable to use a disposable device. Ideally, this device should be compact (as long connectors may limit a user's mobility during use) and light weight; a therapy can last from 5 minutes to 45 minutes. Described herein are devices including gel-pad electrodes with integrated pulse generators and/or controllers for delivering transdermal stimulation (e.g., for TENS, neurostimulation, etc.). These devices may be configured as gel patches that are thin and flexible (similar to an adhesive bandage, such as a Band-Aid) and the pulse generator may be based on a modified LED driver integrated circuit.

For example, FIGS. 1A an 1B show one example a front and back view, respectively, of a non-invasive neuromodulation apparatus (as described in U.S. patent application Ser. No. 16/393590, filed Apr. 24, 2019, and herein incorporated by reference in its entirety). The neuromodulator includes a pulse generator and a microcontroller device that may include transistors to generate the high voltage constant current pulses. The back of the device includes a pair of concentrically arranged electrodes that may couple to the skin through a conductive gel, as shown, and be adhesive held on the skin. As described herein, this apparatus may include a pulse generator that adapts an LED driver integrated circuit.

In general an LED driver integrated circuit (IC) may be extremely small, and may have a very small volume (e.g., around 1 mm$^3$). Thus, a transdermal electrical stimulation device, such as a neuromodulator or a TES apparatus, may be thin, small and lightweight, as well as inexpensive, allowing the device to be configured to be disposable (e.g., configured for single-use or low-number use). The device may also be as flexible a fabric material, allowing it to conform to the skin. Thus, the apparatuses described herein including the LED driver IC based high-voltage pulse generators may form part of a thin, self-adhesive, fabric-based apparatus that may be self-contained to deliver neural modulation and/or TENS.

Typically, the peak power and average power used in TENS and neural modulation are generally low, and therefore these devices may be used with a battery, including using very thin batteries not much thicker than a fabric (e.g., a few mm thick or thinner). Further, the electric current for these apparatuses may be low, in the range of 10 mA to 60 mA, allowing for low-resistance contacts. The apparatuses described herein may use conductive films between a circuit board and the gel (e.g., hydrogel used to make skin contact), rather than soldering, welding, and/or compression electrical contacts. The ease of assembly further reduced the cost of assembly. Further, these LED driver-based apparatuses do not require bulky and tall transformers or inductive couplers to pump up voltages from battery level (typically 3.3 volts) to a voltage around 50 Volts to 60 volts. Instead, the voltages may be pumped up using tiny components that cost very little, and are very thin.

The apparatuses described herein may also be configured to provide precise waveforms that change with time, as may be useful for neural modulation or for TENS. In the past, it was necessary to use expensive and bulky components to achieve arbitrary waveform generation at high voltage. The apparatuses described herein may also detect the skin contact to the patch and start the application of stimulation (e.g., neural modulation) automatically.

TENS applications may apply 50 volts to 60 volts, and may use a larger current of up to 60 mA in order to drive the larger surface area of the gel pads used in TENS. Described herein are methods and apparatuses to achieve high electrical current output with very minimal cost increases by attaching external switches (transistors) to the LED driver IC; these apparatuses may also provide a constant current for the gel patches. The apparatuses described herein may also include (e.g., as part of a TENS and/or neural modulation device), one or more safety protection circuits including (but not limited to) triggering the system to shut down when there is a direct current (DC) at the output instead of short pulses, when the output peak voltage exceeds a target value (e.g., around 60 V, 61 V, 62 V, 63 V, 64 V, 65 V, 66 V, 67 V, 68 V, 69 V, 70 V, etc.). The over-voltage protection pin in the LED driver IC (typically designed to protect the chip from over stressing itself) may be used to provide DC output protection and excessive output voltage shutoff during neural modulation and/or TENS, as described herein.

In some variations, the apparatus may include a pull-tab from the neural modulation gel to the LED driver IC to limit the power consumption after a first use is completed, allowing one or more subsequent uses. In some variations, the patch will remain in that low power state until a first (e.g., outer) layer of gel is removed. Further, the apparatus (which may be referred to in some variations as a "patch") may be configured to detect or confirm skin contact prior to beginning or continuation stimulation. For example, users may activate the device (e.g., patch) before attaching it to the skin with a delay of a few seconds or minutes before it is attached. It is therefore useful to keep the patch in a low-power consumption state until skin contact is confirmed, and not starting to generate the waveforms until the skin contact is made. The apparatuses described herein may use the LED driver IC to determine when the gel is not in touch with skin, and therefore delay the waveform generation until the gel touches skin. In addition or alternatively, these apparatuses may be configured to stop generating waveforms (or delivering waveforms) when the skin contact is interrupted and in some cases resume when the device is reconnected to skin. This may enhance safety as well as for better battery life.

FIG. 2 illustrates one example of a commercially available LED driver IC next to a small Band-Aid for size comparison. The LED driver IC is typically designed to inexpensively convert battery voltage to around 30 volts to drive 5 to 10 LEDs running in series. Generally, the ICs are DC/DC step-up PWM converters that deliver an accurate constant current for driving LEDs. These ICs may operate at a fixed switching frequency of around about 1 MHz allow the device to be used with external ceramic capacitors and inductors. In ordinary operation, LEDs connected in series may be driven with a regulated current set by an external sampling resistor. The ICs are designed for driving a maximum of 30 Volts. An over-voltage protection input measures the output voltage and shuts off the chip if output were to go approximately 20% higher than the expected max voltage.

The LED driver IC may include 5 or more pins. These LED driver ICs may be referred to as step-up DC/DC converters that are designed for driving one or more stings of LEDs from a single battery. These devices typically regulate the output current for driving light emitting diodes (LEDs) whose light intensity is proportional to the current passing through them. Examples of LED driver ICs include (but are not limited to): PT4110 (PowTech), R1208 Series PWM Step-up DCDC converter for White LED (RICOH), and LT3497 (Linear Technology), CAT4137 (ON Semiconductor).

For example, in some variations a first pin (LX pin, switch or SW pin) connects to a tiny inductor to kick up the voltage. A second pin (GND) connects to the ground (battery negative). A third pin (feedback input or FB) is a feedback pin that senses the electrical current going to the LED and cut off the driving transistor when the current exceeds a target value. A fourth pin (enable input, EN or shutdown pin) turns on the chip. When the chip is off, it consumes nearly zero current. A fifth pin (input supply pin or IN) connects to battery positive. In some variations a sixth pin (OVP) protects the chip from excessive voltage. For example, when pin 5 sees over 35 volts, the chip shuts down. Additional, optional pins may be included in some LED driver ICs.

Such LED driver ICs are similar. FIG. 3A is a first block diagram schematically illustrating an LED driver IC. FIG. 3B is a second block diagram schematically illustrating another example of an LED driver IC. At the start of each oscillator cycle, the control logic turns on the power switch M1 (FIG. 3A) to kick up voltages. When this power from M1 reaches the level set by the error amplifier on the left hand side of the block diagram, the PWM comparator turns off the power switch M1 via the control logic. FIG. 3B shows a similar arrangement. In this manner, the error amplifier sets the correct output electrical current level to keep the LED current in regulation. If the feedback voltage at the FB pin starts to drop, the output of the error amplifier increases. This results in more current to flow through M1, hence increasing the power delivered to the output.

Thus, an LED driver IC may include: a power switch device (e.g., M1), an oscillator operating between 1 MHz to 2 MHz, which may switch M1 on/off at approximately that frequency; an error amplifier that reads a feedback voltage and may use that to control the on time and/or off time of the power switch M1; a current sense amplifier that reads the current passing through the switch M1 to keep the current from going beyond the capability of the switch; and control logic to keep the switch M1 operating as designed.

The power switch (M1) in FIGS. 3A-3B is internal to the LED driver IC. In some designs M1 can be external to the LED driver; thus, the power switch may not be essential to the LED driver IC. The current sense amplifier may reads the current passing through the switch (M1) to keep the current from going beyond the capability of the switch, and may decrease the on time of switch M1 when the switch current is too high. Thus, in general, an LED driver may include: an oscillator operating between 1 MHz to 2 MHz driving a switch at approximately that frequency; an error amplifier that reads a feedback voltage and may use that to control the on time and/or off time of the switch; a current sense amplifier that reads the current passing through the switch; and control logic to oversee operation of the switch.

LED driver ICs may sometimes be referred to as "voltage boost IC"; "current regulator IC"; "PWM constant current IC"; and "digital audio amplifier". All these ICs typically include the four basic blocks described above and can adapted for use as the pulse generator for TENS or neural modulation as described herein.

Because of the high level of integration, the LED driver IC typically requires very few external components to function, e.g., when operating to drive LEDs. However, an inductor connecting between the LX pin and the IN pin (battery positive pin) may be included.

Figure 4:
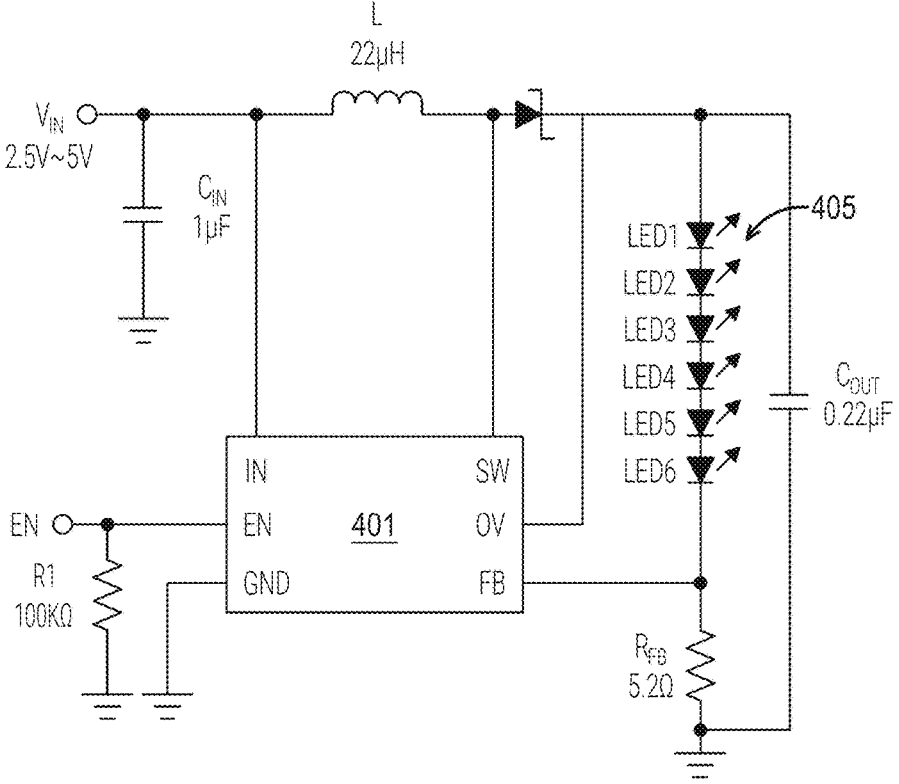
FIG. 4 shows one example of a prior-art circuit for driving a string of LEDs using an LED driver IC.

FIG. 4 shows a typical circuit that allows the LED driver IC to generate 30 Volts DC, with a constant current for lighting LEDs. FIG. 4 illustrates one example of a typical application of an LED driver IC, using Pulse Width Modulation at approximately 1 MHz to raise the voltage from ~3 Volts to ~30 volts with constant current output using feedback to FB pin input. In this example, the chip 401 is shown connected to and driving a chain of LEDs 405.

In operation, when the LED driver IC is coupled to a series of LEDs to drive them as shown in FIG. 4, the LED driver IC provides pulses at the SW pin, coming from the switch M1 inside the chip and switching at approximately 1 MHz, caused the inductor L to kick back a higher voltage at the SW pin. This higher voltage causes current to pass through LED1 to LED6. This LED current passes through $R_{fb}$ (the feedback resistor) to generate a sample voltage to the FB pin. When this sample voltage that represents the LED current exceeds a threshold (typically, e.g., 0.1 V), the switch M1 decreases the power going to the inductor L. However, if there is not enough power from switch M1 to get to the target electrical current, the FB pin will cause switch M1 to provide more power. The OV pin in the LED driver IC connects to the output to monitor the maximum voltage so as to avoid over-exerting the switch M1. This OV pin may be included to avoid the chip being burnt when there is no load present, e.g., without OVP, the LED driver chip will keep pumping up the voltage until it is higher than the switch M1 can tolerate.

The EN pin (the enable pin) in FIG. 4 is in the off position in the circuit shown. Putting a positive voltage to the EN pin turns on the LED driver IC. For example, when used to drive a flashlight, the EN pin typically connects to the flashlight's on/off switch.

Adaption an LED driver IC to Operate as a Neuromodulator Pulse Generator

Figure 5:
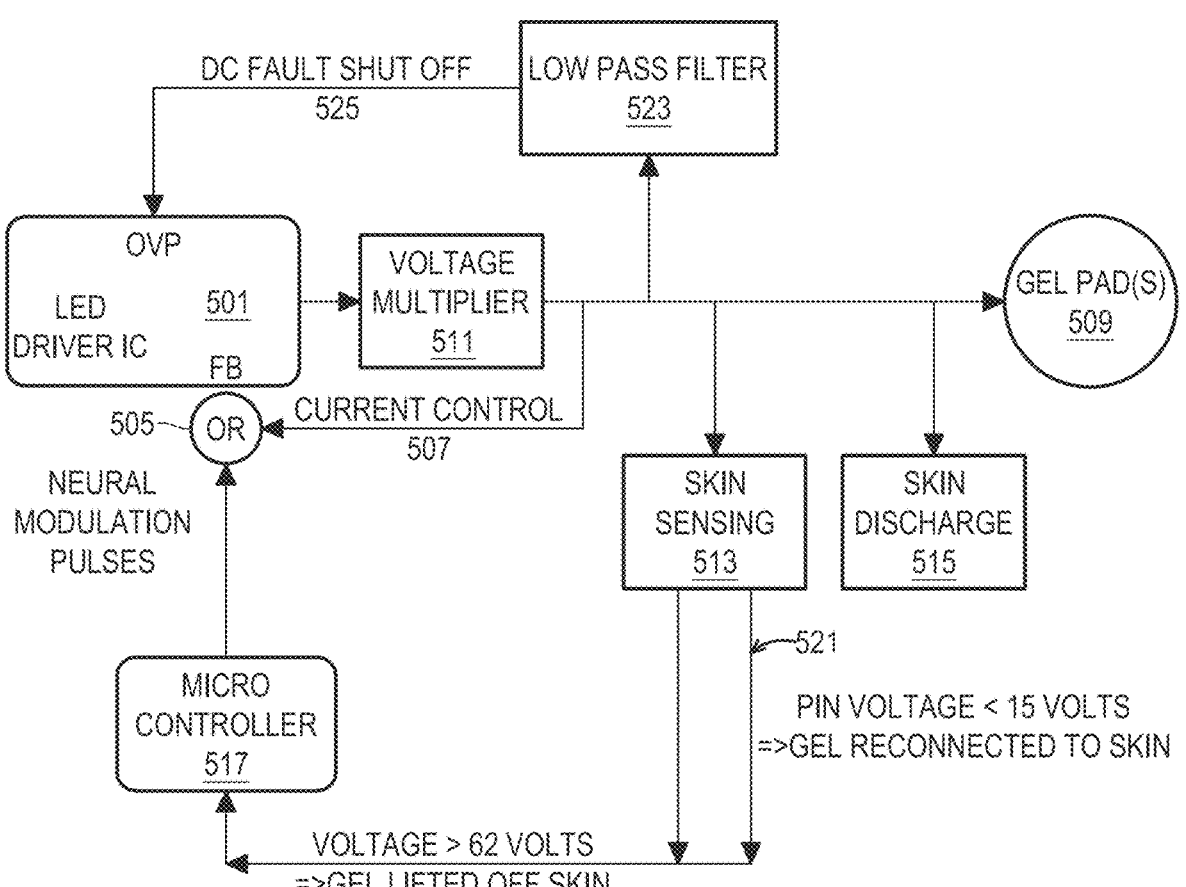
FIG. 5 schematically illustrates one example of a neuromodulator apparatus including an LED driver IC configured to operate as a pulse generator as described herein.

As mentioned, any of the LED driver ICs described herein may be configured as a pulse generator for a neuromodulator, including a TENS device. FIG. 5 illustrates one example of an LED driver IC that is modified by the addition of specific circuits to convert it into a neuromodulator (e.g., neurostimulator, TENS device, etc.) waveform generator, e.g. pulse generator. In FIG. 5, the LED driver IC may be modified by the addition of an electrical "OR" function to the Feedback input of the LED driver IC. In FIG. 5, the OR function 505 is the circle on the bottom of the block representing the LED driver IC 501. The modification to feedback input with an OR function allows the LED driver IC to take 2 inputs: a first input from the micro controller (MC) to modulate the output in accordance to a neural modulation waveform stored in the controller and a second input to sample the output in order to feedback control the output current going to the gel pads 509. The input 507 from the MC in the block diagram of FIG. 5 feeds into the OR gate 505. The second input samples the output in to provide feedback control. In FIG. 5, additional or alternative modifications to the LED driver IC 501 in the block diagram may be external additions, e.g., to convert the LED driver into a neural modulation stimulation wave generator.

Figure 11:
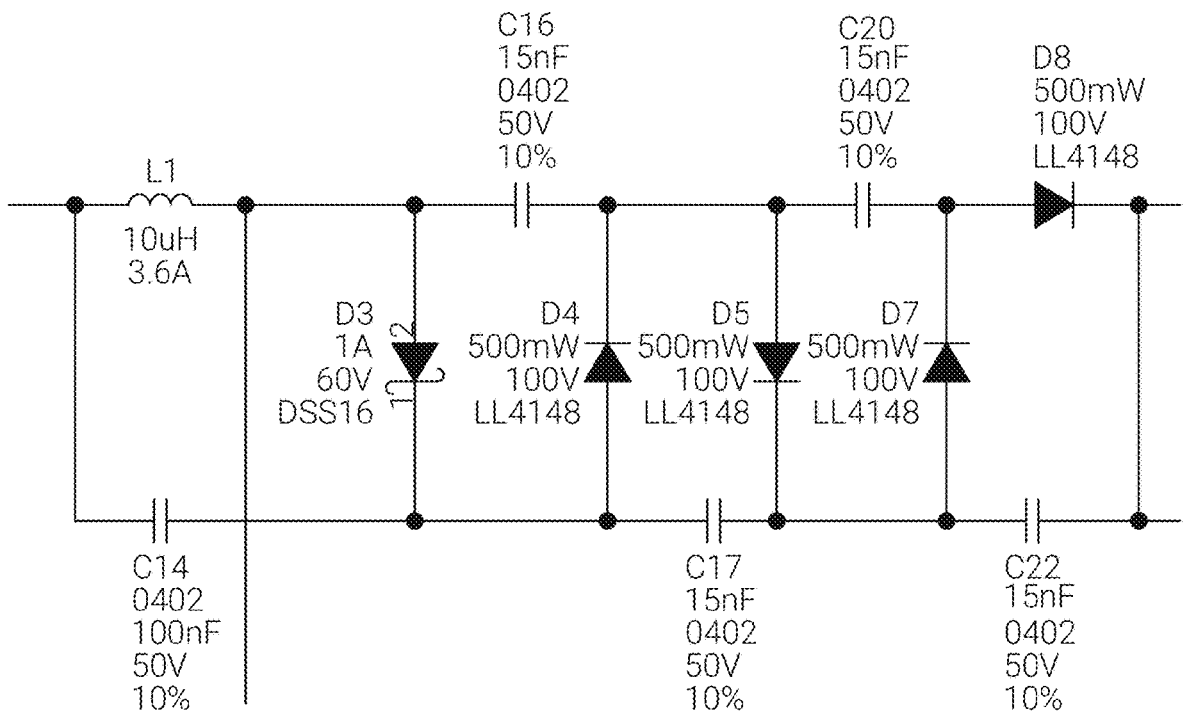
FIG. 11 illustrates one example of a voltage multiplier (e.g., voltage tripler) circuit that may be used as part of a neuromodulator apparatus as described herein.

An addition modification 511 may add voltage multiplier (e.g., voltage tripler) to the output of the LED driver IC, as shown. The voltage tripler 511 may take the output from the LED driver IC to make the voltage 3 times as high (or in the case of a voltage doubler 2×). Any voltage multiplier may be used. An example of a voltage multiplier (e.g., voltage tripler) is shown in FIG. 11, below. In some variations, a high voltage may be needed for transdermal neural modulation or for TENS to overcome the high electrical resistance of the skin to create an electrical field around the nerve fiber bundles to modulate the nerve actions. Thus, any of the apparatuses (e.g., devices and systems, including pulse generators) may include circuitry modifying the LED driver IC to multiply (e.g., double, triple, etc.) the voltage out of the LED driver IC.

Any of the apparatuses descried herein may also discharge capacitive buildup on the skin. For example, in FIG. 5, the apparatus includes a skin discharge 515 circuitry. For example, the LED driver IC may be modified by the addition or circuitry for skin discharge 515. As electrical charge accumulates from the neural modulation pulses applied to the skin where the gel patches 509 meet the skin, it may cause stimulation of surface neurons and cause a minor stinging sensation to the skin. This stimulation is generally harmless, but may be uncomfortable to the user. The cumulated charge may be dissipated in a resistor inside the apparatus (e.g., patch) to improve user comfort.

In some variations, the discharge may be controlled by the microcontroller 517. The discharge may be performed right after the neural modulation pulses or after the TENS pulses were applied to skin.

As mentioned above, any of the apparatuses described herein may be configured to detect and react to the electrodes (e.g., gel pads forming the electrodes) coming off of the skin. For example, the LED driver IC is generally configured to detect a decrease in the load and increase (e.g., pump up) the voltage to try to make the output current hit target level. Described herein are circuits that take advantage of this property of the LED drive IC to determine when the output voltage hits a level higher than expected (due to the LED driver IC detecting a decrease in the load) which is indicative of a decrease in output load, such as when the gel pads are lifted off skin. Voltage sensing (skin sensing 513) may be achieved with one or more Zener diodes, which may start electrical conduction at a designated voltage. For example, the start of conduction of the Zener diode may trigger a signal to the microcontroller to initiate a sequence of events corresponding to the detachment of the gel pads from skin, including switching the output pulses to a very short duration, low voltage "pinging pulse" 521 that allows the gel patch to sense reattachment to skin.

Thus, in some variations, the apparatuses described herein may also be configured so that the LED driver IC is modified to detect skin re-attachment of the gel patches. For example, a "pinging pulse" may be initiated when the patch was first started by pulling a battery pull tab, and/or when the gel patch is detached from skin during a neural modulation session. The pinging pulse generates approximately 20 volts on the gel patches when it is in the air. When the gel patch is re-attached to skin; the pinging pulse may drop to approximately 15 volts due to the load. A second Zener diode detects this transition in voltage, and send the signal to the micro-controller 517 to initiate a neural modulation session.

These modifications may help achieve an automatic start, stop, and/or restart function without requiring manual switches or a user interface on the patch, making the patch much more intuitive to use.

Any of the apparatuses described herein may also adapt the LED driver IC to protect the user against DC fault conditions. For example, any of these apparatuses may be modified by coupling the LED driver IC's Voltage Protection (OVP) input into a direct current (DC) voltage sensor to protect the user against DC fault condition coming from the electronics. Typically TENS or neural modulation uses very short pulses to achieve the results. When the output instead puts out a direct current, it is in a fault state and should be shut down to protect the user against direct current effects. By adding a low pass filter 523 to the OVP input of the LED driver IC, the LED driver IC becomes sensitive to direct current at the output, and may shut down the LED driver when DC is present 525. Thus, the apparatus (e.g., patch) may be prevented from functioning when the OVP is tripped. This modification allows the LED driver to protect the user without added costs, by adapting the LED driver IC's over-voltage pin.

Figure 6:
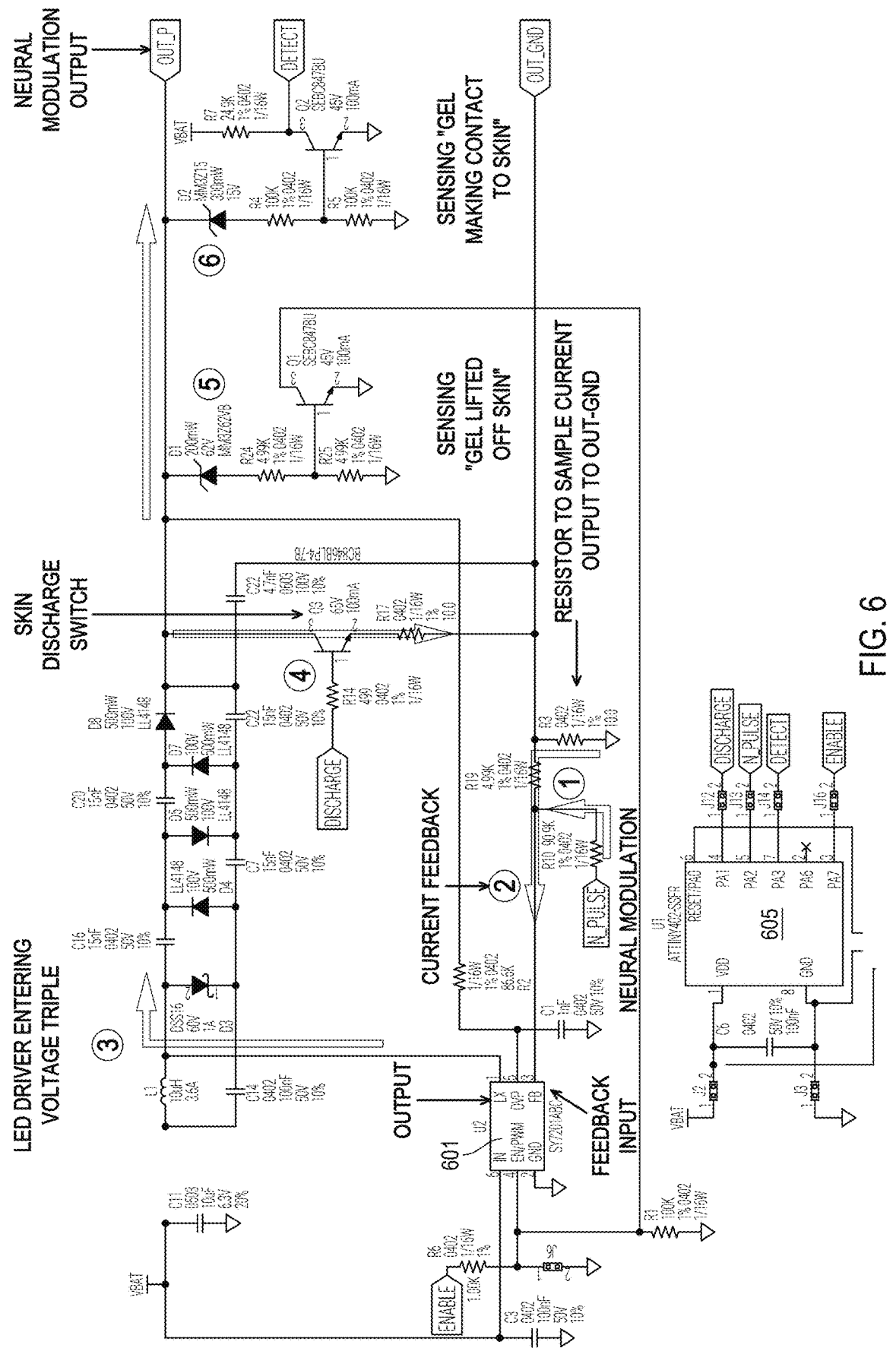
FIG. 6 is a circuit schematic of a neuromodulator apparatus including an LED driver IC configured to operate as a pulse generator as described herein.

FIG. 6 illustrates one example of an apparatus including an LED driver IC with examples of circuits configured to adapt the LED driver IC as discussed above, shown as external wiring in order to convert it into a Neural modulation/TENS waveform generator. In FIG. 6 the IC chip 601 includes pins coupled to (1) the receive input from the micro controller to modulate the output in accordance to the neural modulation waveform stored in the controller, fed into the feedback pin ("neuralmodulation") or (2) to sample the output in order to feedback control the output current going to the gel pads ("current feedback"). FIG. 6 also illustrates an example of a voltage multiplier (3), fed into the input pin ("voltage tripler"). The LED driver IC is also coupled to circuitry forming a skin discharge switch (4). A sensing circuit (5) couples to the overvoltage protection pin of the LED driver IC (sensing the electrode off of the skin), and a skin discharge circuit (6) senses the contact between the gel and the skin. In FIG. 6, the U1 is the microcontroller 605; U2 is the LED driver 601; D3 to D7 are diodes for the voltage tripler. Q5 and Zener D11 detects the sudden rise of output voltage beyond 65 volts that indicates gel pads are in the air. Q3 discharges skin current upon command from the micro-controller.

For example, the LED driver IC may be modified by injection of a neural modulation sequence into the Feedback pin of the LED driver. As described in FIG. 5, above, the micro controller may store the inverse of a neural modulation wave sequence for play back, e.g., through output pin PA2 in FIG. 6. This control signal is called the N-Pulse.

Figure 7:
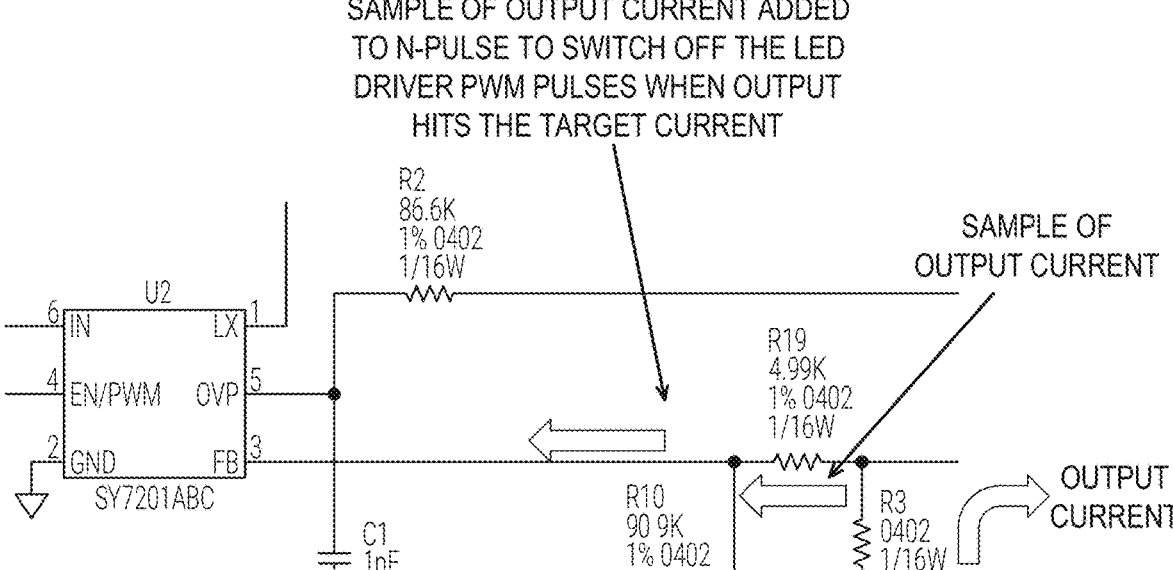
FIG. 7 illustrates a portion of a neuromodulator apparatus as described herein, showing the electrical communication between the LED driver IC and a neuromodulator waveform from the microcontroller (N-pulse) as well as a sample of the output current. The sample of output current, e.g., from an output of the voltage multiplier, is added to the N-pulse from the microcontroller to switch off the LED driver IC PWM pulses when the output hits a target current; the LED driver IC's output is switched on and off according to the inverse of the N-pulse signal.

The N-Pulse connects to the Feedback input pin of the LED driver IC (FB). Through this connection, The LED driver IC's output signal forms an inverted, magnified version of the N-Pulse signal. In the schematic, this connection is shown as arrow #1 in FIG. 6; this portion is shown in greater detail in FIG. 7. FIG. 7 shows details of the modified input to the feedback pin (FB). This pin with the modifications shown may switch off the PWM pulses to decrease output when one of 2 conditions are met: first, if the N-pulse is high, or second, if the output current exceeds a set threshold. Thus, FIG. 7 shows details of the OR function added to the LED driver IC so that the IC output decreases when N-pulse signal from the micro controller is high, or when the output current exceeds a threshold value.

Figure 8:
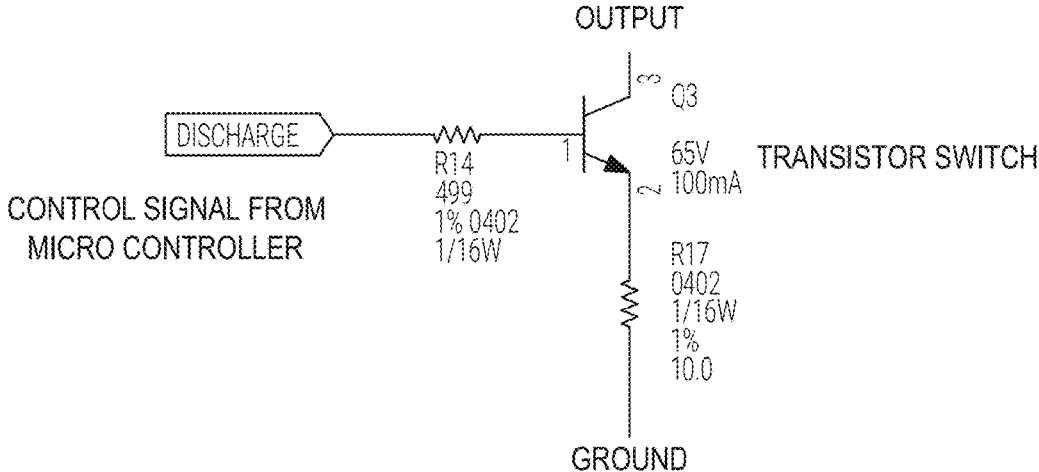
FIG. 8 illustrates an optional portion neuromodulator apparatus as described herein, showing circuitry permits the LED driver IC to achieve constant current pulses at the LED driver output through a modification that adds a sample of the neural modulation current to the feedback pin of the LED driver IC.

A second modification is illustrated in greater detail in FIG. 8, showing the circuitry that may permit the LED driver IC to achieve constant current pulses at the LED driver output with a modification that adds a sample of the neural modulation current to the feedback pin of the LED driver IC. This connection is indicated by the arrow (2) in the schematic of FIG. 6. The neural modulation output (at OUT_P in the schematic of FIG. 6) follows the neural modulation sequence as described for the first modification, above, and at the same time may hold the output pulse current constant at a targeted level of electric current, typically ~20 mA. This may be achieved by an electrical "OR" function implemented at the Feedback input of the LED driver IC, labeled as FB. The electrical "OR" may mean connecting both the first modification and the second modification together at the Feedback input, so that the output is modulated either by the stored sequence, or when the output electric current exceeds the target level.

The third modification is to (optionally) multiply the voltage, e.g., by including a voltage multiplier, such as a voltage doubler or voltage tripler, to the output of the LED driver IC, as shown in FIG. 6 and in greater detail in FIG. 11. In some variations the output range (e.g., approximately 20-25 V) of the LED driver IC may be sufficient for driving neuromodulation without further voltage multiplication. In FIG. 6, the arrow (3) illustrates this.

As shown in the example of FIG. 11, the alternating current (AC) output of the LED controller IC may fill the capacitors C14, C17, C22 with voltages from the LED driver coil L1. C14 may be filled through the diodes D3. C17 may be filled through the diodes D3, D4 & D5; C22 may be filled through the diodes D3, D4, D5, D7 & D8. The 3 capacitors C14, C17, C22 are shown connected in series. Therefore the voltages on them are additive. If the LED driver IC produces a voltage V, then the three voltages from the three capacitors add up to 3V, achieving a tripling of voltages. For example, C14 has one side of it connected to ground through $V_{batt}$. The other side connects to C17, and C17 connects to C22 in this example. The other side of C22 connects to the positive output OUT_P. Therefore OUT_P has 3 times the voltage coming out of the LED driver IC. The diodes inject voltages into each capacitor without allowing the energy from leaking back to the source, similar to a one-way valve for filling each of the 3 series capacitors.

The fourth modification of the LED driver IC in FIG. 6 is the addition of skin discharge to the output of the LED driver IC. In this example, a switch is added to the output of the LED driver after the voltage tripler. This switch Q3 is controlled by the micro controller and discharge the electrical charges cumulated on the skin periodically to help eliminate the pinching sensation on skin due to charge accumulation. This is shown in greater detail in FIG. 8, illustrating details of the skin discharge switch controlled by the micro controller. FIG. 8 shows a skin discharge switch added to LED driver IC.

Figure 9:
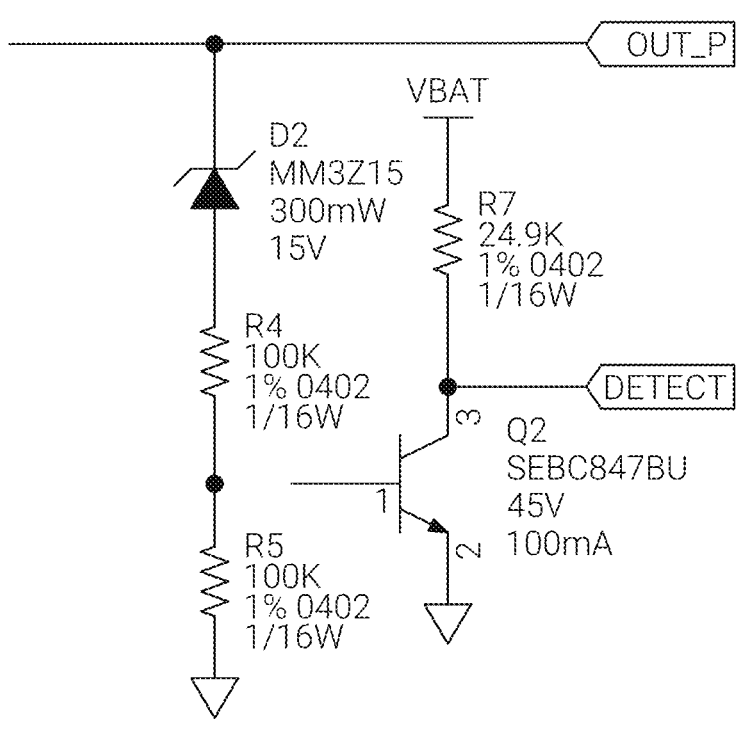
FIG. 9 illustrates an optional portion neuromodulator apparatus as described herein, showing voltage sensor circuitry that may adapt the LED driver output to react when the electrode(s) (e.g., a gel pad) is lifted off of the skin during a neural modulation session.

FIG. 9 illustrates one example of a fifth modification of the LED driver IC, showing the addition of a voltage sensor to the LED driver output to sense when the electrode(s) (e.g., a gel pad) is lifted off of the skin during a neural modulation session. The LED driver IC may continue to raise the output voltage when there is no load connected to it, based on the normal operation of the LED driver IC. Taking advantage of this property, the LED driver IC may be adapted to sense when the gel pad is lifted off of the skin during a neural modulation session based on this continuous raise in the output voltage. For example, when the gel pad is lifted off of the skin, the voltage output may rise to 65 volts, or even 75 volts if there is no moisture on the gel pads. This rise in output voltage may be sensed with a Zener diode, e.g., rated at around 62 volts. A transistor Q1 may be added to serve to interface the voltage sensing to the micro controller for action. When the micro controller senses the gel pad lifting off skin, it may be configured to ramp down the neural modulation pulses, and switch to pulses of substantially shorter duration. These shorter pulses, which may be referred to as "pinging pulses", consume very little energy. They are pinging to sense the re-attachment of the gel pads to skin. The ramping down of pulses is a safety measure to avoid the gel pads making contact to other parts of the body that may be sensitive to electrical impulses.

If the electrode (e.g., gel pad) does not get re-attached to skin after a period of time (from 30 minutes to a few hours), the micro controller will instruct the LED driver IC to go to sleep to further reduce power consumption, then put itself to sleep too. The system may awaken again when a clip switch is actuated when a "gel separator tab" is being removed in the gel stack. FIG. 9 shows additional detail for the voltage sensor modification. In FIG. 9, the Zener diode D2 sets the voltage that conduction starts. When the output voltage "Out_P" is below the set voltage, the diode does not conduct. When the output voltage exceeds the diode voltage, electrical conduction starts, and a current passes thru R4 and R5. Q2 picks up this voltage when the current is strong enough and sends a "detect" signal to the micro controller's Input pin. Based on this signal, the micro-controller initiates a sequence of activities required to keep the gel pad operating once the gel contacts skin. Thus, FIG. 9 shows one example of an output voltage sensor modification of the LED driver IC to operate as a pulse generator of a neuro-modulator/TEC apparatus.

A sixth modification may include the addition of a second voltage sensor to the LED driver output to sense the gel pad attachment to skin. For example, when an electrode (gel patch) is first initiated for use, the micro controller may immediately send very short "pinging pulses" to the gel patch to sense when the gel attaches to skin. These pulses may be so short that the voltage on the gel pad is less than 20 volts even if the gel pads are in air. However, once the gel makes contact with skin, the skin conductivity of electricity will decrease the voltages to less than 15 volts. A second voltage sensor may be coupled to the LED driver IC output to sense this lower voltage that represents the gel patch getting a skin contact. This is very similar to the fifth modification, as shown in FIG. 9, except that the Zener diode threshold voltage is around 15 volts. When the micro controller senses the gel pads are attached to skin, by the voltage of this sensor going from a high value (e.g., >15 volts) to a low value (e.g., <15 volts), it ramps up the output pulses according to the needs of neural modulation.

In any of the apparatuses described herein, the LED driver IC may be modulated to follow a prescribed waveform for TENS or for neural modulation. This may be achieved by adapting the voltage at the feedback input (FB pin) which determines the output electrical current. For example, at zero Volts, the output may be the maximum current. When voltage at FB exceeds 0.1 Volt, the output current would be driven to zero. Thus applying the inverse of the neural modulation waveform at the FB pin modulates the output current as desired.

Thus, in any of the variations described herein the LED driver IC may be coupled at the feedback input (e.g., FB pin) to an inverted and normalized (e.g., between 0 and 100 mV) signal corresponding to the current waveform. The inverse waveform may be stored or generated by a micro-controller IC, as described herein. This controller IC may be approximately the same size as the LED driver IC (e.g., very thin and small). Since the inverse signal is typically generated by firmware code, there is no additional cost to the TENS modulation of the LED driver. The micro-controller may be very small and thin, and may therefore allow a disposable patch to be very thin, and very light weight. Applying TENS modulation at the feedback input of LED driver IC may also provide for the constant current capability typically required by neural modulation and/or TENS.

Further, in any of the apparatuses described herein, the power consumption may be kept low because the LED driver IC consumes power only when there is a pulse needed for neural modulation. This may be achieved by having the LED driver driven to completely turn off the internal switch M1 when there is no TENS pulse required. The LED controller IC may be power efficient during the pulse on-time, typically achieving 92% efficiency or better. Since there is no power consumption during pulse off-time, and approximately 92% efficiency during pulse on time, the overall battery efficiency is close to 92%. Through a combination of the above, majority of the energy from the battery is used for the actual neural modulation with very little waste.

Figure 10:
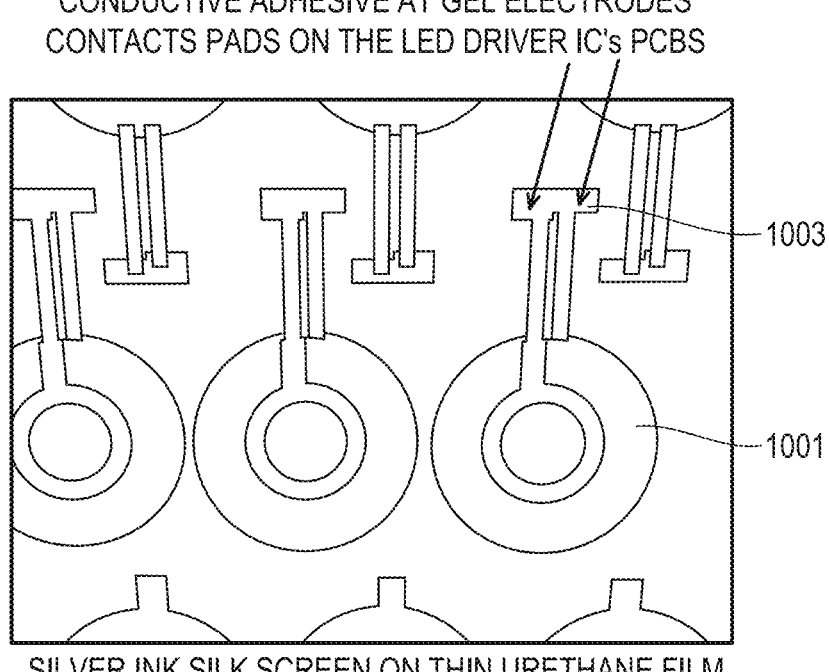
FIG. 10 illustrates one example of an adhesive connector between a gel electrode and the LED driver IC.

In any of the apparatuses described herein the electrical connections from the gel patch to the LED controller IC's output may be made using conductive adhesives having substantially lower cost as compared to traditional wired TENS. Traditional TENS gel pads are expensive because they have to use high quality, very flexible wires to go from the box to the gel pads, or the wires may pull on the gel pads causing detachment from the skin. In a disposable system, these wires are thrown away after a couple of uses, and may be expensive, often gold plated, because an unreliable connection may be painful for the user. These connectors are also thrown away after a few uses. In the disposable patches described herein, the connection from the gel pad to the LED driver IC may use a conductive adhesive film. By integrating the IC to the gel pads, the costs of inter-connect may be reduced. Thus, any of the apparatuses described herein may advantageously and surprisingly reliably use a conductive adhesive film to connect the electrode gel pad (e.g., hydro-gel) to the LED driver IC. For example, FIG. 10 illustrates one example of an adhesive connection from the gel 1001 to the LED driver to an IC's Pads 1003. In FIG. 10, an example of a low cost adhesive connection from gel patch to LED driver IC's printed circuit board is shown.

As described above, any of the apparatuses in which an LED driver IC is adapted for use as part of the pulse generator, a voltage multiplier (e.g., doubler or tripler) circuit may be used to pump up the LED driver output to 60 volts. The LED driver IC typically does not go to a high voltages of 50 or 60 Volts. FIG. 11 shows one example of a voltage tripler circuit that triples the voltage from an LED driver IC using 5 diodes and 5 capacitors. In FIG. 11 the voltage tripler circuit shown has an input on the left and output on the right. When connected to the LED driver's Switch M1 output (the SW pin), the voltage tripler increases the voltage by 2× or 3×. This circuit can provide a high current output only when the frequency is high (like 1 MHz), therefore only useful when working in conjunction with the LED driver ICs of high frequency. A tripler circuit, along with the high frequency used in the LED driver IC, provides the high voltages and current for TENS or neural modulation. The circuit is extremely thin when SMT (surface mount technology) components are used, typically around 0.3 mm thick. Traditional methods of using transformers or coupled inductors to raise voltages are 10 times as thick, and cost a lot more.

Any of the apparatuses described herein may be used to delivery an arbitrary waveform from the adapted LED driver ICs. For example, although an LED driver IC was not designed to create arbitrary waveforms for TENS or for neural modulation, through the connection of the Feedback input (FB pin) to a micro-controller I/O pin, an LED driver IC may be used to generate arbitrary waveforms.

Figure 12:
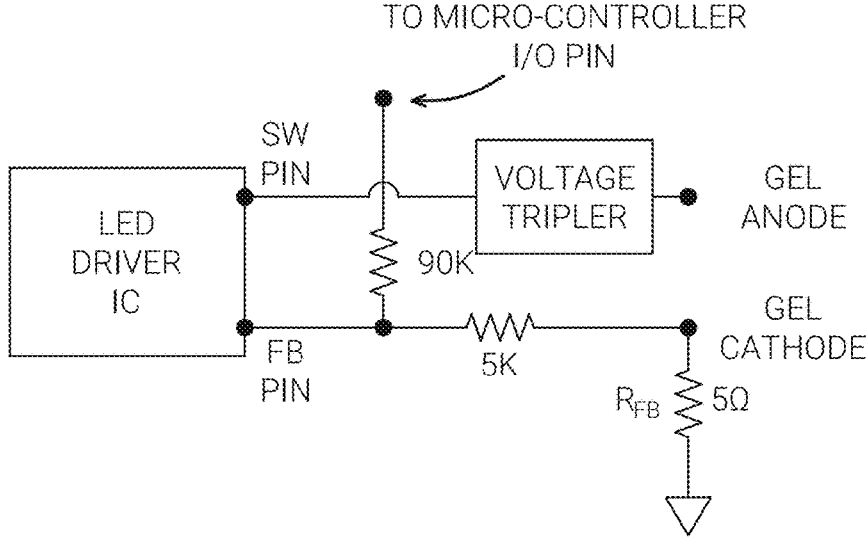
FIG. 12 is an example of an electrical "OR" arrangement, where the LED driver output current is made to follows both the micro-controller's I/O pin control and the sampling of output current from feedback resistor, Rth.

FIG. 12 shows one example of an electrical "OR" arrangement, where the LED driver output current is made to follows both the micro-controller's I/O pin control and the sampling of output current from feedback resistor, Rth. This may be achieved by connecting the Feedback pin (FB pin) to the low cost micro-controller's I/O pin in a "logic OR" arrangement, formed (in this example) by the 90K resistor and the 5K resistor, which allowed the modulation of the LED driver to provide arbitrary waveforms stored in the micro-controller.

In any of the apparatuses described herein an LED driver IC may be adapted to detect if the electrode (e.g., gel) is in air or is in contact with the skin. For example, a Zener diode may be connected to the output of the voltage tripler. The Zener diode may start conducting after the Zener threshold is reached, which may be approximately 65 volts. This high voltage condition may signify that the gel is in air. The LED driver IC may keep pumping up the voltage until a target value of electrical current is achieved. When the gel is in air, the impedance is high without the conductivity of the skin and the LED driver IC will pump up the voltage to try reach the target current. This high voltage will trip the Zener diode. A sampling resistor connected in series with the Zener diode will trigger an I/O pin of the microcontroller, which signifies that the gel is in air. When the gel makes skin contact, the Zener diode current goes from high to low due to output voltage going back down.

Figure 13:
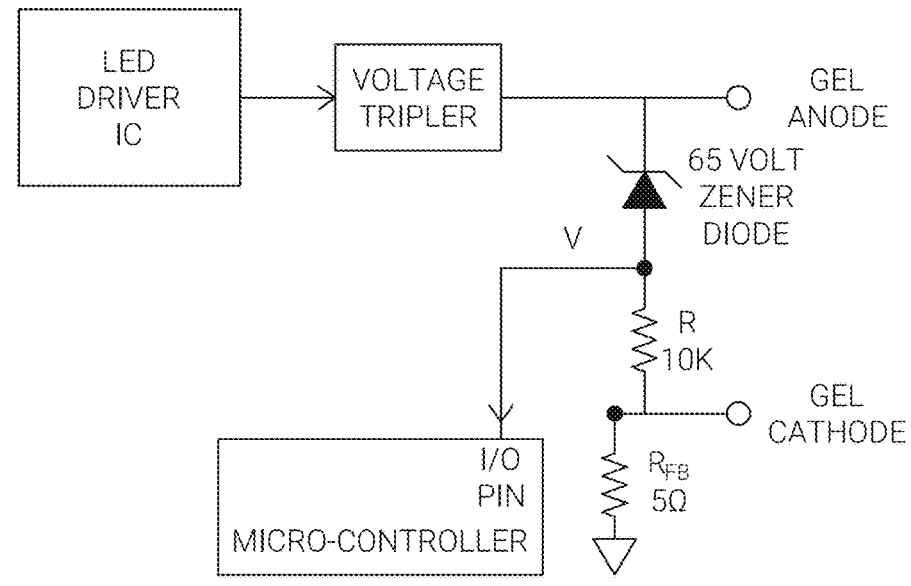
FIG. 13 shows one example of a circuit showing a connection between the LED driver IC and a Zener diode to provide on-air/on-skin detector.

FIG. 13 shows one example of a circuit showing a connection between the LED driver IC and a Zener diode to provide on-air/on-skin detector. In FIG. 13, the off-skin detection using the conduction of the 65 volts Zener diode may be used to signal to the micro-controller that the gel is in air.

Figure 14:
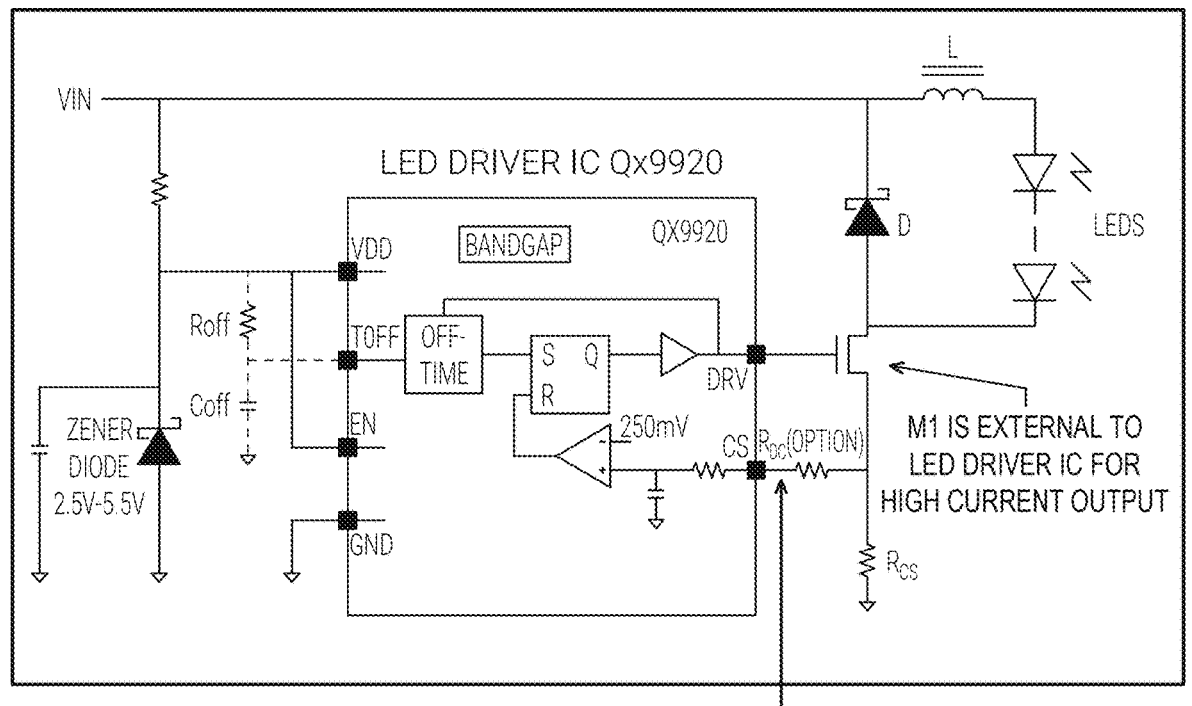
FIG. 14 is one example of an apparatus having a switch (M1) that is external to the driver IC to increase the maximum current output.

In any of the apparatuses described herein the LED driver IC may be configured to provide a high electrical current output which may be particularly useful for TENS, e.g., by using a switch element external to the LED driver IC. The higher output current may be achieved by having the switch M1 external to the LED driver IC. The IC in this variation may retain the essential blocks described previously, with the exception of switch M1. The switch being external to the LED driver chip allows better heat dissipation and much higher switch current. An example is IC QX9920 widely used in flashlights. In this example a higher power switch element M1 may be used to deliver a higher light output when driving LEDs. The external components may be used (current limit protection and over voltage protection are now external to the IC) and the driver IC does not provide the power switch component. A schematic example of one variation having an external M1 design is shown in FIG. 14. FIG. 14 shows an example of an apparatus having a switch M1 external to the driver IC to increase the maximum current output for applications such as TENS. Thus, in some variations, the apparatus may include a mechanism providing constant current for TENS or neural modulation with zero added cost to the high voltage generator.

The apparatus may be configured to sample the current going to the gel pad by adding a small resistor in series with the gel connection. This sample of the electrical current goes to the feedback input of the LED driver IC to maintain constant current during the pulse on time. The sampling location may be after the voltage multiplier (e.g., voltage tripler) so that gel electrode current is directly measured. The LED driver IC can also deliver constant voltage if needed. For example, in some cases the neural modulation effects may be stronger if the skin capacitance is charged up with constant current first, followed by constant voltage to drive more coulombs through the skin resistance.

The apparatuses described herein may be configured as efficient mechanism for storing complex neural modulation waveforms within a tiny micro-controllers. Representations of complex time-variable waveforms may be stored in a compact form using, e.g., segment descriptions rather than point by point. The method used very little memory, and may be used herein (e.g., storage of complex wave sequences in a micro-controller).

Figure 15:
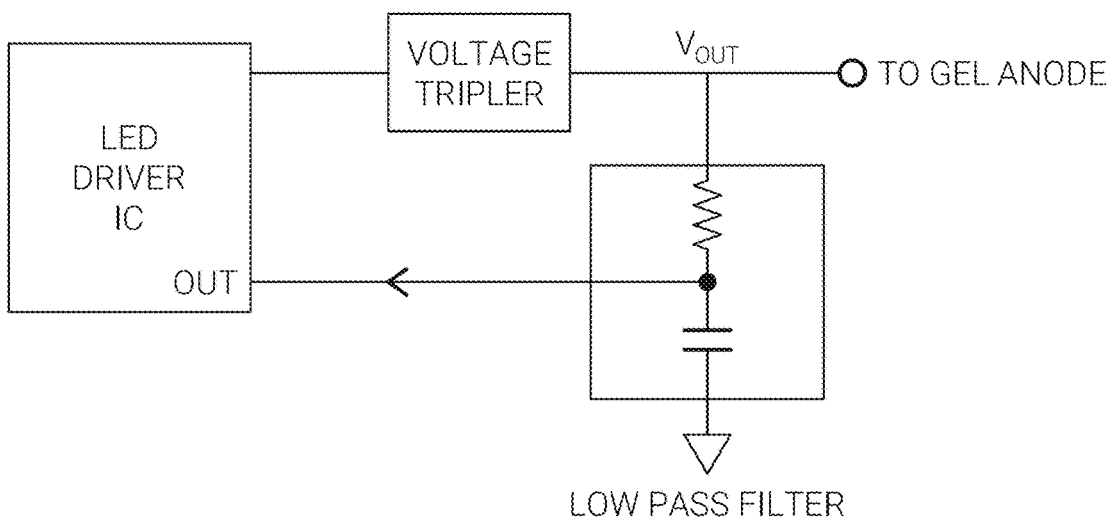
FIG. 15 is an example of a circuit that may enhance user safety protection at very low cost by connecting the OVP (over voltage protection) sense input in the LED driver IC to the gel pad through a low pass filter.

These method and apparatuses may generally be safer than other transdermal stimulators. For example, in a disposable patch the OVP sensing input of the LED driver IC may be connected through a low pass filter to the gel electrodes. If the patch were to generate a DC voltage at the gel, the low pass filter will let the DC pass through to trip the OVP. Normal neural modulation pulses, or TENS Pulses, are rejected by the low pass filter so that they will not trip the OVP. See, e.g., FIG. 15 showing the connection of OVP detection via low pass filter to the electrode (e.g., gel). The low pass filter typically consists of a resistor and a capacitor connected as shown, but can be other configurations.

LED driver ICs may have an Over Voltage Protection (OVP) feature to shut down the system when the LED is removed. This OVP input may trips at, e.g., 35 volts, around 5 volts higher than the targeted maximum output voltage in the LED driver IC. This OVP feature is typically included in the IC to avoid over-stressing the switch M1 when there is no load. As described above, voltage output may continue to rise when there is very little current drawn at the output; the increased voltage is the IC's attempt to deliver the target current. FIG. 15 shows a circuit that may enhance user safety protection at very low cost by connecting the OVP (over voltage protection) sense input in the LED driver IC to the gel pad through a low pass filter.

Figure 16:
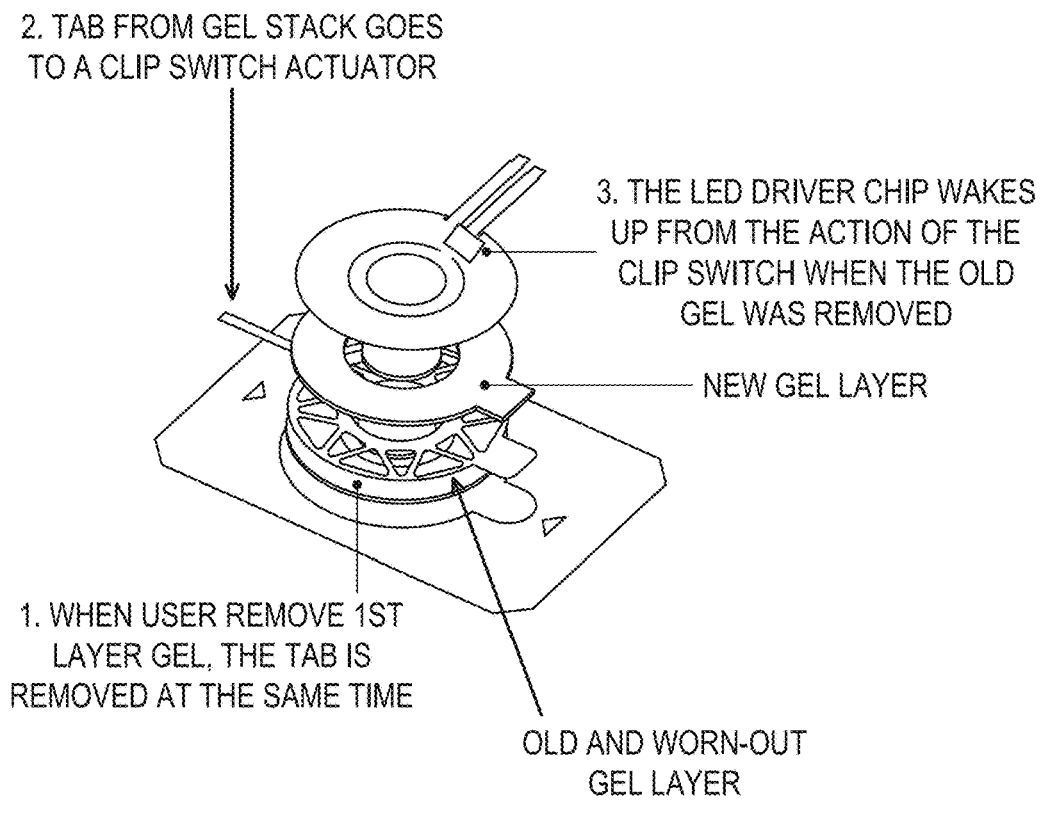
FIG. 16 is a schematic illustration showing an exploded view of one variation of an apparatus including a pair of hydrogel electrode layers that may be sequentially used (and the first, outer layer removed after use to expose the new, second layer) in which the LED driver IC is adapted to detect removal of the first out gel layer and exposure of the second, new layer.

As mentioned, the apparatuses described herein may have close to zero power consumption between uses without the need of a power switch. When the neural modulation session ends, or shortly after, the micro-controller may put the LED driver IC into sleep mode by taking away the voltage on the enable input of the LED IC (the EN pin). The sleep mode consumes close to zero power. The microcontroller then goes to sleep to preserve power. In variations having multiple disposable gel layers (see, e.g., FIG. 16), when the user disposes of the old gel by pulling on a separator layer, the action trips a tiny clip switch. This switch wakes up the micro-controller and the LED driver chip. FIG. 16 illustrates one example of a mechanical arrangement configured in this manner. In FIG. 16, a mechanical diagram shows the actuation of the LED driver IC when a used gel layer was removed.

Thus, in any of these variations, the apparatus may shut off output when the gel is removed from skin to provide safety protection. This safety mechanism may help avoid an active gel patch sticking to parts of the body that are sensitive to the electrical pulses. The same Zener diode mechanism described above for the sixth modification may provide on-air detection. The transition of on-skin to on-air may trigger output shut-off. The micro-controller may be responsible for the logic to shut off the neural modulation waveform. Shut off may be achieved by using a much shorter pulse (e.g., approximately 4% duration of a TENS pulse) on the gel. The shorter pulse may allow the detection of the subsequent re-attachment of the gel to skin.

Thus, in some variations, the apparatus may have a reduced power consumption when the gel patch is in air and not touching skin. The waveform output may go into a much shorter pulse (e.g., approximately 4% duration or less) when gel is detected to be in air. The shorter pulse duration reduced power consumption substantially since the PWM mechanism of the LED driver IC consumes almost no power when not putting out energy. The Zener diode mechanism described above may provide on-skin detection when user reattaches the gel patch to skin. The waveform may resume a normal duration needed for neural modulation or TENS upon on-skin detection.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A neuromodulator apparatus comprising:
an electrode pair;
a microcontroller storing one or more neural modulation waveform parameters;
an LED driver integrated circuit (IC) adapted to function as a pulse generator, wherein a first pin of the LED driver IC is in electrically communication with a first electrode of the electrode pair, and a feedback pin on the LED driver IC is coupled to the microcontroller to modulate an output of the LED driver IC on the first pin in accordance to the one or more neural modulation waveform parameters stored in the microcontroller; and a voltage multiplier circuit in electrical communication with the first pin and the first electrode so that the voltage multiplier circuit multiplies a voltage output of the LED driver IC delivered before the first electrode; wherein the output from the LED driver IC is modulated by the microcontroller and output by the first electrode.

2. The apparatus of claim 1, wherein the voltage multiplier circuit is configured to multiple a voltage from the LED driver IC to greater than 50 V.

3. The apparatus of claim 1, wherein the voltage multiplier circuit comprises a voltage doubler or a voltage tripler.

4. The apparatus of claim 1, wherein the LED driver IC comprises an oscillator having an operating frequency between 1 MHz to 2 MHz configured to drive a switch at the operating frequency, an error amplifier that reads a feedback voltage to control on time and off time of the switch, a current sense amplifier that reads a current passing through the switch to keep the current from going beyond a capability of the switch, and control logic.

5. The apparatus of claim 4, wherein the LED driver IC further comprises the switch.

6. The apparatus of claim 1, wherein the electrode pair comprises a pair of hydrogel skin contacts.

7. The apparatus of claim 1, further comprising an OR gate on the feedback pin of the LED driver IC, wherein the OR gate receives input from the microcontroller and from a sample input that is in electrical communication with the first electrode.

8. The apparatus of claim 1, further comprising skin discharge circuitry in electrical communication with the microcontroller, configured to discharge capacitive energy from skin during or after neuromodulation is applied to the skin.

9. The apparatus of claim 1, further comprising a skin detection circuit coupled to a pin on the LED driver IC, wherein the skin sensing circuit is configured to detect contact with skin based on an output voltage of the LED driver IC.

10. The apparatus of claim 9, wherein the skin detection circuit is configured to trigger a signal to the microcontroller to switch output pulses from the LED driver IC to a short duration, low-voltage pinging pulses when a voltage from the LED driver IC exceeds a threshold.

11. The apparatus of claim 10, wherein the skin detection circuit is further configured to detect contact with skin when a voltage of the low-voltage pinging pulses falls below a threshold voltage.

12. The apparatus of claim 1, further comprising a low pass filter in electrical communication with an OVP pin of the LED driver IC, wherein the apparatus is configured to shut down the LED driver IC when a DC is detected.

13. The apparatus of claim 1, further wherein the microcontroller is configured to store an inverse of a neural modulation wave sequence that is between 0 mV and 100 mV, for application to the feedback pin of the LED driver IC.

14. The apparatus of claim 1, further wherein the first electrode comprises a conductive adhesive film electrically coupling a first gel electrode pad to the first pin.

15. The apparatus of claim 1, wherein an output of the LED driver IC to the first pin is an AC output.

16. The apparatus of claim 1, wherein the LED driver IC further comprises an enable pin in electrical communication with the microcontroller, wherein the apparatus is configured to modulate the enable pin when a neuromodulation frequency is between about 0.1 HZ to 100 HZ.

17. A neuromodulator apparatus comprising:

an electrode pair;

a microcontroller storing one or more neural modulation waveform parameters; and an LED driver integrated circuit (IC) adapted to function as a pulse generator, wherein a first pin of the LED driver IC is in electrically communication with a first electrode of the electrode pair, and a feedback pin on the LED driver IC is coupled to the microcontroller to modulate an output of the LED driver IC on the first pin in accordance to the one or more neural modulation waveform parameters stored in the microcontroller;

wherein the output from the LED driver IC is an AC output and is modulated by the microcontroller and output by the first electrode.

18. A neuromodulator apparatus comprising:

an electrode pair;

a microcontroller storing one or more neural modulation waveform parameters;

an LED driver integrated circuit (IC) adapted to function as a pulse generator, wherein a first pin of the LED driver IC is in electrically communication with a first electrode of the electrode pair, and a feedback pin on the LED driver IC is coupled to the microcontroller to modulate an output of the LED driver IC on the first pin in accordance to the one or more neural modulation waveform parameters stored in the microcontroller; and skin discharge circuitry in electrical communication with the microcontroller, the skin discharge circuitry configured to discharge capacitive energy from skin during or after neuromodulation is applied to the skin;

wherein the output from the LED driver IC is modulated by the microcontroller and output by the first electrode.

19. A neuromodulator apparatus comprising:

an electrode pair, wherein the electrode pair comprises a pair of hydrogel skin contacts;

a microcontroller storing one or more neural modulation waveform parameters; and an LED driver integrated circuit (IC) adapted to function as a pulse generator, wherein a first pin of the LED driver IC is in electrically communication with a first electrode of the electrode pair, and a feedback pin on the LED driver IC is coupled to the microcontroller to modulate an output of the LED driver IC on the first pin in accordance to the one or more neural modulation waveform parameters stored in the microcontroller;

wherein the output from the LED driver IC is modulated by the microcontroller and output by the first electrode.

* * * * *